(12) United States Patent
Kim

(10) Patent No.: US 11,771,742 B2
(45) Date of Patent: Oct. 3, 2023

(54) NANO-VESICLES DERIVED FROM GENUS CUPRIAVIDUS BACTERIA AND USE THEREOF

(71) Applicant: MD HEALTHCARE INC., Seoul (KR)

(72) Inventor: Yoon-Keun Kim, Paji-Si (KR)

(73) Assignee: MD HEALTHCARE INC., Seoul (KR)

( * ) Notice: Subject to any disclaimer, the term of this patent is extended or adjusted under 35 U.S.C. 154(b) by 288 days.

(21) Appl. No.: 17/029,711

(22) Filed: Sep. 23, 2020

(65) Prior Publication Data

US 2021/0008157 A1    Jan. 14, 2021

Related U.S. Application Data

(63) Continuation-in-part of application No. 16/563,594, filed on Sep. 6, 2019, now abandoned, which is a continuation of application No. PCT/KR2019/002015, filed on Feb. 20, 2019.

(30) Foreign Application Priority Data

Feb. 21, 2018    (KR) .................. 10-2018-0020573
Feb. 19, 2019    (KR) .................. 10-2019-0018989

(51) Int. Cl.
*A61K 38/16*    (2006.01)
*C07K 14/195*    (2006.01)
*C07K 16/28*    (2006.01)
*A61K 9/00*    (2006.01)

(52) U.S. Cl.
CPC .......... *A61K 38/164* (2013.01); *A61K 9/0073* (2013.01); *C07K 14/195* (2013.01); *C07K 16/2818* (2013.01); *C07K 16/2827* (2013.01); *C07K 16/2878* (2013.01)

(58) Field of Classification Search
None
See application file for complete search history.

(56) References Cited

U.S. PATENT DOCUMENTS

| | | |
|---|---|---|
| 2013/0089530 A1 | 4/2013 | Rodriguez |
| 2019/0177783 A1 | 6/2019 | Kim |
| 2019/0345561 A1 | 11/2019 | Kim et al. |

FOREIGN PATENT DOCUMENTS

| | | |
|---|---|---|
| JP | 2017-517569 A | 6/2017 |
| KR | 10-2011-0025068 A | 3/2011 |
| KR | 10-2016-0073157 A | 6/2016 |
| KR | 10-2017-0015958 A | 2/2017 |
| KR | 10-2018-0006303 A | 1/2018 |
| WO | 2017/009693 A1 | 1/2017 |
| WO | 2018/008895 A1 | 1/2018 |
| WO | 2018/030732 A1 | 2/2018 |

OTHER PUBLICATIONS

Mak et al. Lost in translation: animal models and clinical trials in cancer treatment. Am. J. Transl. Res. 6(2):114-118. (Year: 2014).*
Singh et al. Modeling and predicting clinical efficacy for drugs targeting the tumor milieu. Nature Biotechnology 30(7): 648-657. (Year: 2012).*
Morgan, R. Human Tumor Xenografts: The Good, the Bad, and the Ugly. Molecular Therapy 20(5): 882-884. (Year: 2012).*
Kim et al. Drug Efficacy Testing in Mice. Curr. Top. Microbiol. Immunol. 355: 19-38. (Year: 2012).*
Van der Worp et al. Can Animal Models of Disease Reliably Inform Human Studies? PLOS Medicine 7(3): e1000245 (pp. 1-8). (Year: 2010).*
Leal et al. Interleukin-1β and tumor necrosis factor-α: reliable targets for protective therapies in Parkinson's Disease? Frontiers in Cellular Neuroscience 7, Article 53 (10 pages). (Year: 2013).
Steeland et al. A new venue of TNF targeting. International Journal of Molecular Sciences 19, 1442 (55 pages). (Year: 2018).
Balakumar et al. Anti-tumour necrosis factor-α therapy in heart failure: future directions. Basic & Clinical Pharmacology & Toxicology 99:391-397. (Year: 2006).
Kang et al. Extracellular Vesicles Derived from Gut Microbiota, Especially Akkermansia muciniphila, Protect the Progression of Dextran Sulfate Sodium-Induced Colitis. PLOS One 8(10):e76520 (11 pages). (Year: 2013).
Choi et al. Gut microbe-derived extracellular vesicles induce insulin resistance, thereby impairing glucose metabolism in skeletal muscle. Scientific Reports 5:15878 (11 pages). (Year: 2015).
Yoo et al. 16S rRNA gene-based metagenomic analysis reveals differences in bacteria-derived extracellular vesicles in the urine of pregnant and non-pregnant women. Experimental & Molecular Medicine 48:e208 (8 pages). (Year: 2016).
Park et al. Metagenome analysis of bodily microbiota in a mouse model of Alzheimer disease using bacteria-derived membrane vesicles in blood. Experimental Neurobiology 26(6):369-379. (Year: 2017).
Taciak et al. Evaluation of phenotypic and functional stability of RAW 264.7 cell line through serial passages. PLOS One 13(6): e0198943 (13 pages). (Year: 2018).

(Continued)

*Primary Examiner* — Samuel C Woolwine
(74) *Attorney, Agent, or Firm* — Vorys, Sater Seymour and Pease LLP; Mih Suhn Koh

(57) ABSTRACT

The present invention relates to vesicles derived from bacteria belonging to the genus *Cupriavidus* and a use thereof, the vesicles derived from bacteria belonging to the genus *Cupriavidus* may be usefully used for the purpose of developing a method of diagnosing a malignant diseases such as gastric cancer, colon cancer, pancreatic cancer, cholangiocarcinoma, breast cancer, ovarian cancer, bladder cancer, prostate cancer, head and neck cancer, lymphoma, and the like, heart diseases such as cardiomyopathy, atrial fibrillation, variant angina, and the like, chronic obstructive pulmonary disease, stroke, diabetes, kidney failure, dementia, Parkinson's disease, or depression, and a composition for preventing or treating the diseases.

8 Claims, 38 Drawing Sheets

Specification includes a Sequence Listing.

(56) References Cited

OTHER PUBLICATIONS

Castle et al. Immunomic, genomic and transcriptomic characterization of CT26 colorectal carcinoma. BMC Genomics 15:190 (12 pages). (Year: 2014).

Van der Worp et al. Can animal models of disease reliably inform human studies? PLOS Medicine 7(3):e1000245 (8 pages). (Year: 2010).

The extended European search report for corresponding European application No. 19745027.3, dated Aug. 4, 2020, 11 pages.

The office action for corresponding Japanese application No. 2019-548319, dated Sep. 15, 2020, 16 pages.

The final rejection for corresponding Japanese application No. 2019-548319, dated Mar. 30, 2021, 14 pages.

EPO Machine Translation of WO2018030732A1, 2018, 25 pages.

D'Inzeo et al., "Catheter-related bacteremia by Cupriavidus metallidurans", Diagnostic Microbiology and Infectious Disease, 2015, vol. 81, pp. 9-12.

Langevin et al., "First Case of Invasive Human Infection Caused by Cupriavidus metallidurans", Journal of Clinical Microbiology, 2011, vol. 49, No. 2, pp. 744-745.

Lin et al., "Differential miRNA expression in pleural effusions derived from extracellular vesicles of patients with lung cancer, pulmonary tuberculosis, or pneumonia", Tumor Biol., 2016, vol. 37, pp. 15835-15845.

Xu et al., "Native and Foreign Proteins Secreted by the Cupriavidus metallidurans Type II System and an Alternative Mechanism", J. Microbiol. Biotechnol., 2017, vol. 27, No. 4, pp. 791-807.

Matsueda et al., "Immunotherapy in gastric cancer", World J Gastroenterol, 2014, 20(7): 1657-1666.

Timmerman et al., "Dendritic Cell Vaccines for Cancer Immunotherapy", Annu. Rev. Med., 1999, 50:507-529.

\* cited by examiner

NANO-VESICLES DERIVED FROM GENUS CUPRIAVIDUS BACTERIA AND USE THEREOF

CROSS-REFERENCE TO RELATED APPLICATION

This application is a Continuation-in-Part of U.S. patent application Ser. No. 16/563,594, filed Sep. 6, 2019, which was a Continuation Application of PCT/KR2019/002015, filed Feb. 20, 2019, which claims the benefit of priority from Korean Patent Application No. 10-2018-0020573, filed Feb. 21, 2018 and Korean Patent Application No. 10-2019-0018989, filed Feb. 19, 2019, the contents of each of which are incorporated herein by reference in its entirety.

SEQUENCE LISTING

The Sequence Listing submitted in text format (.txt) filed on Sep. 23, 2020, named "SequenceListing.txt", created on Sep. 6, 2019 (742 bytes), is incorporated herein by reference.

TECHNICAL FIELD

The present invention relates to nanovesicles derived from bacteria belonging to the genus *Cupriavidus* and a use thereof, and more particularly, to a method of diagnosing cancer, cardiovascular disease, lung disease, metabolic disease, neuropsychiatric disorders by using nanovesicles derived from bacteria belonging to the genus *Cupriavidus*, and the like, a composition for preventing, alleviating, or treating the above-listed diseases, which comprises the nanovesicles, and the like.

BACKGROUND ART

Since the beginning of the 21st century, acute infectious diseases recognized as epidemic diseases in the past have become less important, whereas chronic diseases accompanied by immune dysfunction caused by disharmony between humans and microbiomes have changed disease patterns as main diseases that determine the quality of life and the human lifespan. Cancer, cardiovascular disease, chronic lung cancer, metabolic disease, neuropsychiatric disorders, and the like, which are intractable chronic diseases in the $21^{st}$ century, have become major problems in public health, and these intractable chronic diseases are characterized by chronic inflammation accompanied by immune dysfunction due to causative factors.

It is known that the number of microorganisms coexisting in the human body has reached 100 trillion, which is 10 times more than the number of human cells, and the number of microorganism genes is more than 100 times the number of human genes. A microbiota or microbiome refers to a microbial community including bacteria, archaea and eukarya present in a given habitat.

Bacteria coexisting in our body and bacteria present in the ambient environment secrete nanometer-sized vesicles in order to exchange information on genes, low molecular compounds, proteins, and the like with other cells. The mucosa forms a physical defense membrane through which particles having a size of 200 nanometers (nm) or more cannot pass, so that bacteria coexisting in the mucosa cannot pass through the mucosa, but vesicles derived from bacteria have a size of 100 nanometers or less and are absorbed into our bodies after relatively freely passing through epithelial cells via the mucosa.

Locally secreted bacterial-derived vesicles not only are absorbed through mucosal epithelial cells or skin keratinocytes to induce local inflammatory responses but also are absorbed into our bodies to be distributed to respective organs and regulate immune and inflammatory responses in the organ that absorbs the vesicles. For example, vesicles derived from pathogenic Gram-negative bacteria such as *Escherichia coli* are inhaled through the airway to induce pulmonary emphysema, thus inducing chronic obstructive pulmonary disorder (COPD), locally induce colitis when absorbed via the intestine, and promote systemic inflammatory responses and blood coagulation through vascular endothelial cell inflammatory responses in blood vessels. In addition, such vesicles are absorbed into muscle cells on which insulin acts, and the like to cause insulin resistance and diabetes. In contrast, vesicles derived from beneficial bacteria may regulate diseases by regulating immune functions dysfunctions by pathogenic vesicles.

As immune response to factors such as bacteria-derived vesicles and the like, a Th17 immune response characterized by secretion of the interleukin (IL)-17 cytokine occurs where IL-6 is secreted when exposed to bacteria-derived vesicles, thus inducing the Th17 immune response. Inflammation by the Th17 immune response is characterized by neutrophil infiltration, and in a process where inflammation occurs, tumor necrosis factor-alpha (TNF-α), which is secreted from inflammatory cells such as macrophages, neutrophils, and the like, plays an important role in the development of a disease.

Bacteria belonging to the genus *Cupriavidus* are aerobic Gram-negative bacilli that are isolated from soil and clinical specimens. Among these, *Cupriavidus metallidurans* is known to be resistant to toxic heavy metals, produce energy through oxidative phosphorylation, and generally have no pathogenicity. In addition, bacteria belonging to the genus *Cupriavidus* such as *Cupriavidus necator* and *Cupriavidus taiwanensis* are known to fix nitrogen in leguminous plants. However, it has not been reported that bacteria belonging to the genus *Cupriavidus* extracellularly secrete vesicles, and particularly, there is no report of application thereof to the diagnosis and treatment of intractable diseases such as cancer, cardiovascular disease, lung disease, metabolic disease, neuropsychiatric disorders, and the like.

DISCLOSURE

Technical Problem

As a result of having conducted intensive studies to address the above-described conventional problems, the inventors of the present invention confirmed through metagenomic analysis that the content of vesicles derived from bacteria belonging to the genus *Cupriavidus* was significantly reduced in samples derived from patients with malignant diseases such as gastric cancer, colon cancer, pancreatic cancer, cholangiocarcinoma, breast cancer, ovarian cancer, bladder cancer, prostate cancer, head and neck cancer, lymphoma, and the like, heart diseases such as cardiomyopathy, atrial fibrillation, variant angina, and the like, chronic obstructive pulmonary disease, stroke, diabetes, kidney failure, dementia, Parkinson's disease, or depression, compared to samples of normal individuals. It was also confirmed that, when isolating vesicles from *C. metallidurans*, which is a bacterium belonging to the genus *Cupria-*

*vidus* and treating macrophages therewith, the secretion of IL-6 and TNF-α by pathogenic vesicles was significantly inhibited and this treatment also has an anticancer effect in a mouse model, thus completing the present invention based on these findings.

Thus, an object of the present invention is to provide a method of providing information for diagnosing gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, or depression.

Further, another object of the present invention is to provide a composition for preventing, alleviating or treating gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, or depression, comprising bacteria belonging to the genus *Cupriavidus*-derived vesicles as an active ingredient.

However, a technical problem to be achieved by the present invention is not limited to the aforementioned problems, and the other problems that are not mentioned may be clearly understood by a person skilled in the art from the following description.

Technical Solution

To achieve the object of the present invention as described above, the present invention provides a method of providing information for diagnosis of gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, or depression, the method comprising the following steps:
  (a) extracting DNAs from extracellular vesicles isolated a normal individual sample and a subject sample;
  (b) performing polymerase chain reaction (PCR) on the extracted DNA using a pair of primers prepared based on a gene sequence present in 16S rDNA to obtain each PCR product; and
  (c) classifying a case in which a content of extracellular vesicles derived from bacteria belonging to the genus *Cupriavidus* is lower than that of the normal individual sample, as gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, or depression, through quantitative analysis of the PCR product.

In addition, the present invention provides a method of diagnosing gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, or depression, the method comprising the following steps:
  (a) extracting DNAs from extracellular vesicles isolated a normal individual sample and a subject sample;
  (b) performing polymerase chain reaction (PCR) on the extracted DNA using a pair of primers prepared based on a gene sequence present in 16S rDNA to obtain each PCR product; and
  (c) classifying a case in which a content of extracellular vesicles derived from bacteria belonging to the genus *Cupriavidus* is lower than that of the normal individual sample, as gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, or depression, through quantitative analysis of the PCR product.

As an exemplary embodiment of the present invention, the sample in Step (a) may be stool, blood, urine, or saliva.

As another exemplary embodiment of the present invention, the primer pair in Step (b) may be primers of SEQ ID Nos. 1 and 2.

Further, the present invention provides a pharmaceutical composition for preventing or treating gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, or depression, comprising vesicles derived from bacteria belonging to the genus *Cupriavidus* as an active ingredient.

In addition, the present invention provides a food composition for preventing or alleviating gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, or depression, comprising vesicles derived from bacteria belonging to the genus *Cupriavidus* as an active ingredient.

In addition, the present invention provides an inhalant composition for preventing or treating gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, or depression, comprising vesicles derived from bacteria belonging to the genus *Cupriavidus* as an active ingredient.

Furthermore, the present invention provides a method of preventing or treating gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, or depression, the method comprising a step of administering a pharmaceutical composition comprising vesicles derived from bacteria belonging to the genus *Cupriavidus* as an active ingredient to a subject.

Further, the present invention provides a use of vesicles derived from bacteria belonging to the genus *Cupriavidus* for preventing or treating gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, or depression.

As an exemplary embodiment of the present invention, the vesicles may have an average diameter of 10 to 200 nm.

As another exemplary embodiment of the present invention, the vesicles may be secreted naturally or artificially from bacteria belonging to the genus *Cupriavidus*.

As another exemplary embodiment of the present invention, the vesicles derived from bacteria belonging to the genus *Cupriavidus* may be vesicles derived from *Cupriavidus metallidurans*.

Advantageous Effects

The present inventors confirmed that intestinal bacteria are not absorbed into the body, but vesicles derived from bacteria are absorbed into the body through epithelial cells, systemically distributed, and excreted from the body through the kidneys, liver, and lungs, and that through a metagenomic analysis of vesicles derived from bacteria present in the stool, blood, urine, or saliva, and the like of a patient, vesicles derived from bacteria belonging to a genus *Cupriavidus* present in the stool, blood, urine, or saliva of patients with gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, or depression had been significantly decreased as compared to those in normal individual. It was also confirmed that, when culturing *Cupriavidus metallidurans*, which is a bacterium belonging to the genus *Cupriavidus* in vitro and isolating vesicles therefrom, and then administering the isolated vesicles to inflammatory cells in vitro, the secretion of an inflammatory mediator by pathogenic vesicles was significantly inhibited, and thus it is anticipated that vesicles derived from bacteria belonging to the genus *Cupriavidus* can be effectively used in a method of diagnosing gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, or depression, and a composition for preventing, alleviating, or treating the above-described disease.

DESCRIPTION OF DRAWINGS

FIGS. 2A to 2C illustrate results of comparing the distribution of vesicles derived from bacteria belonging to the genus *Cupriavidus* after metagenomic analysis of bacteria-derived vesicles present in gastric cancer patients and normal individuals, wherein FIG. 2A illustrates results using stool samples, FIG. 2B illustrates results using blood samples, and FIG. 2C illustrates results using urine samples.

FIGS. 3A and 3B illustrate results of comparing the distribution of vesicles derived from bacteria belonging to the genus *Cupriavidus* after metagenomic analysis of bacteria-derived vesicles present in colon cancer patients and normal individuals, wherein FIG. 3A illustrates results using stool samples, and FIG. 3B illustrates results using urine samples.

FIGS. 6A and 6B illustrate results of comparing the distributions of vesicles derived from bacteria belonging to the genus *Cupriavidus* after metagenomic analysis of bacteria-derived vesicles present in breast cancer patients and a normal individuals, wherein FIG. 6A illustrates results using blood samples, and FIG. 6B illustrates results using urine samples.

FIGS. 7A and 7B illustrate results of comparing the distributions of vesicles derived from bacteria belonging to the genus *Cupriavidus* after metagenomic analysis of bacteria-derived vesicles present in ovarian cancer patients and a normal individuals, wherein FIG. 7A illustrates results using blood samples, and FIG. 7B illustrates results using urine samples.

FIGS. 8A and 8B illustrate results of comparing the distributions of vesicles derived from bacteria belonging to the genus *Cupriavidus* after metagenomic analysis of bacteria-derived vesicles present in bladder cancer patients and a normal individuals, wherein FIG. 8A illustrates results using blood samples, and FIG. 8B illustrates results using urine samples.

FIGS. 12A to 12C illustrate results of comparing the distribution of vesicles derived from bacteria belonging to the genus *Cupriavidus* after metagenomic analysis of bacteria-derived vesicles present in blood samples of heart disease patients and normal individuals, wherein FIG. 12A illustrates the case of cardiomyopathy, FIG. 12B illustrates the case of atrial fibrillation, and FIG. 12C illustrates the case of variant angina.

FIGS. 15A to 15C illustrate results of comparing the distributions of vesicles derived from bacteria belonging to the genus *Cupriavidus* after metagenomic analysis of bacteria-derived vesicles present in diabetes patients and a normal individuals, wherein FIG. 15A illustrates results using blood samples, FIG. 15B illustrates results using urine samples, and FIG. 15C illustrates results using saliva samples.

BEST MODE

Figure 1A:
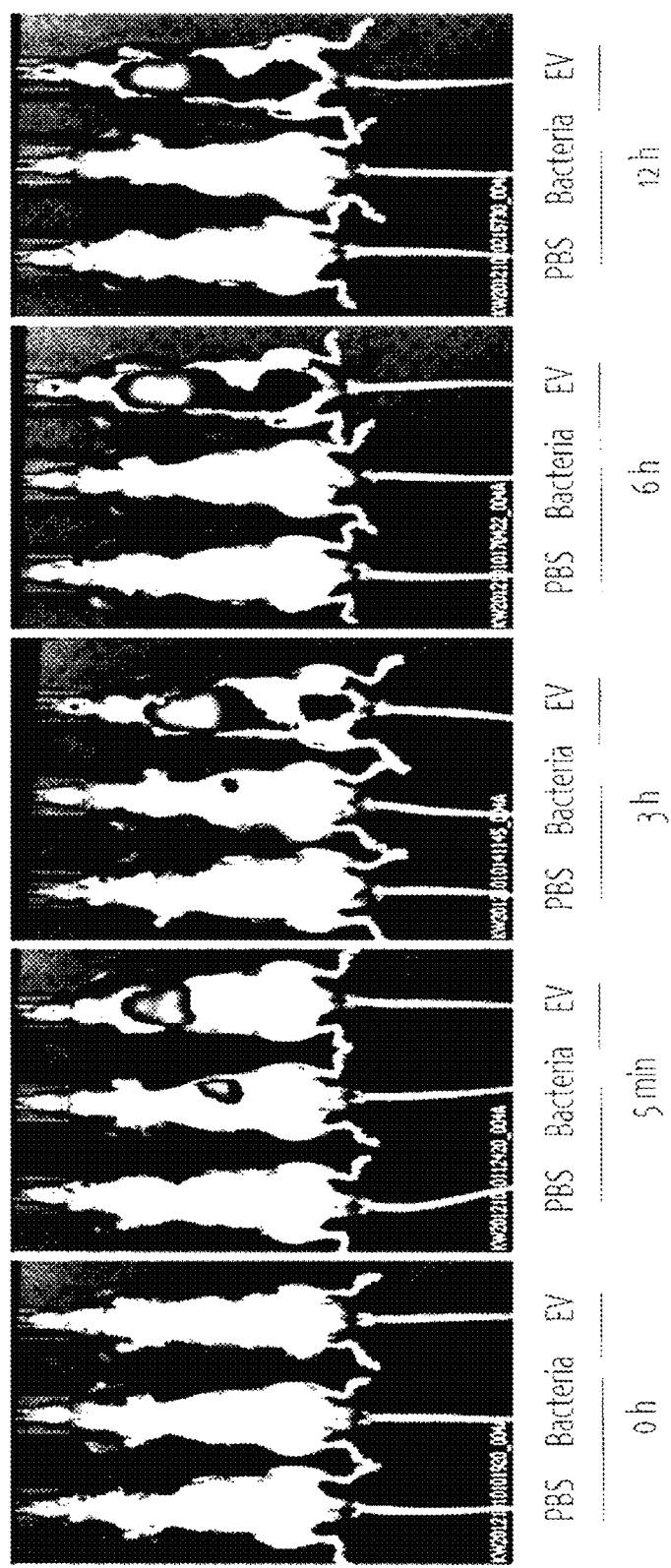
FIG. 1A is a series of photographs capturing distribution patterns of bacteria and vesicles derived from bacteria (EV) by time after the bacteria and the vesicles derived from bacteria were orally administered to mice.

The present invention relates to vesicles derived from bacteria belonging to the genus *Cupriavidus* and a use thereof.

The inventors of the present invention confirmed through metagenomic analysis that the content of vesicles derived from bacteria belonging to the genus *Cupriavidus* was significantly reduced in clinical samples of patients with cancer, cardiovascular disease, lung disease, metabolic disease, and neuropsychiatric disorders, and thus the diseases could be diagnosed. It was also confirmed that, as a result of first isolating vesicles from *C. metallidurans* and characterizing the isolated vesicles, the strain-derived vesicles were able to regulate immune dysfunction due to pathogenic vesicles, inflammation, and cancer.

Thus, the present invention provides a method of providing information for diagnosing gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, or depression, the method comprising the following steps:
   (a) extracting DNAs from extracellular vesicles isolated a normal individual sample and a subject sample;
   (b) performing polymerase chain reaction (PCR) on the extracted DNA using a pair of primers prepared based on a gene sequence present in 16S rDNA to obtain each PCR product; and
   (c) classifying a case in which a content of extracellular vesicles derived from bacteria belonging to the genus *Cupriavidus* is lower than that of the normal individual sample, as gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, or depression, through quantitative analysis of the PCR product.

The term "diagnosis" as used herein refers to determination of a condition of a disease of a patient over all aspects, in a broad sense. The contents of the determination are the disease entity, the etiology, the pathogenesis, the severity, the detailed aspects of a disease, the presence and absence of complications, the prognosis, and the like. The diagnosis in the present invention means determining whether gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, and/or depression occur, the level of the disease, and the like.

In the present invention, the sample may be stool, blood, urine, or saliva, but is not limited thereto.

The term "metagenome" as used herein also refers to a microbiome, and refers to a total of genomes including all viruses, bacteria, fungi, and the like in an isolated region such as soil and an animal's intestines, and is typically used as a concept of genomes explaining identification of a large number of microorganisms at one time by using a sequence analyzer in order to analyze uncultivated microorganisms. In particular, the metagenome does not refer to a genome of one species, but refers to a kind of mixed genome as a genome of all species of one environmental unit. The metagenome is, when one species is defined in the development process of omics biology, a term derived from the viewpoint of making a complete species is made by various species interacting with each other as well as one kind of functionally existing species. Technically, the metagenome is an object of a technique to identify all species in one environment and investigate interactions and metabolism by analyzing all DNAs and RNAs regardless of species using a rapid sequence analysis method.

As another aspect of the present invention, the present invention provides a composition for preventing, treating, or alleviating gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, and/or depression, comprising vesicles derived from bacteria belonging to the genus *Cupriavidus* as an active ingredient. The composition comprises a food composition, an inhalant composition, and a pharmaceutical composition, and in the present invention, the food composition comprises a health functional food composition. In addition, the composition of the present invention may be formulated into an oral spray, a nasal spray, or an inhalant.

The term "immune check point blocking agent" as used herein refer to agents for cancer immunotherapy. The immune check point blocking agent can block inhibitory checkpoints, restoring immune system function in cancer. In particular, the immune check point blocking agent is selected from the group consisting of anti-PD-1, anti-PD-L1, anti-CTLA-4, anti-B7-H4, anti-B7-H1, anti-LAG3, BTLA, anti-Tim3, anti-B7-DC, anti-CD160, anti-4-1BB, anti-OX40, anti-CD27, and CD40 agonist antibodies.

The term "prevention" as used herein refers to all actions that suppress the diseases or delay the onset thereof via administration of the composition according to the present invention.

The term "treatment" as used herein refers to all actions that alleviate or beneficially change symptoms of the diseases via administration of composition according to the present invention.

The term "alleviation" used as used herein refers to all actions that at least reduce a parameter associated with a condition to be treated, for example, the degree of symptoms.

The term "nanovesicle" or "vesicle" as used herein refers to a structure consisting of a nano-sized membrane secreted from various bacteria.

Vesicles derived from gram-negative bacteria or outer membrane vesicles (OMVs) have not only endotoxins (lipopolysaccharides) but also proteins, low molecular compounds, and bacterial DNA and RNA, and vesicles derived from gram-positive bacteria also have peptidoglycan and lipoteichoic acid which are cell wall components of bacteria in addition to proteins, low molecular compounds, and nucleic acids. In the present invention, nanovesicles or vesicles are secreted naturally from bacteria belonging to the genus *Cupriavidus* or produced artificially, are in the form of a sphere, and have an average diameter of 10 to 200 nm.

The vesicles may be isolated from a culturing solution comprising bacteria belonging to the genus *Cupriavidus* by using one or more methods selected from the group consisting of centrifugation, ultra-high speed centrifugation, high pressure treatment, extrusion, sonication, cell lysis, homogenization, freezing-thawing, electroporation, mechanical decomposition, chemical treatment, filtration by a filter, gel filtration chromatography, free-flow electrophoresis, and capillary electrophoresis. Further, a process such as washing for removing impurities and concentration of obtained vesicles may be further included.

In one embodiment of the present invention, as a result of orally administering bacteria and bacteria-derived vesicles to mice and observing in vivo absorption, distribution, and excretion patterns of the bacteria and the vesicles, it was confirmed that, while the bacteria were not absorbed via the intestinal mucous membrane, the bacteria-derived vesicles were absorbed within 5 minutes after administration and systemically distributed, and excreted via the kidneys, liver, and the like (see Example 1).

In another exemplary embodiment of the present invention, a bacterial metagenomic analysis was performed by using vesicles isolated from the stool, blood, urine, or saliva of normal individuals who were matched in age and sex with patients with gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, and depression, and the like. As a result, it was confirmed that vesicles derived from bacteria belonging to the genus *Cupriavidus* were significantly decreased in samples of patients with gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, and depression as compared to samples of normal individuals (see Examples 3 to 20).

In another embodiment of the present invention, as a result of further having conducted research to characterize vesicles derived from *Cupriavidus metallidurans*, which is a bacterium belonging to the genus *Cupriavidus* based on the above-described example results, evaluating whether vesicles secreted from the cultured *Cupriavidus metallidurans* strain exhibited an anti-inflammatory effect, and evaluating the secretion of inflammatory mediators after treating macrophages with *Cupriavidus metallidurans*-derived vesicles at various concentrations, and then treating the macrophages with *E. coli*-derived vesicles, which are a causative factor of inflammatory diseases, it was confirmed that the *Cupriavidus metallidurans*-derived vesicles efficiently inhibited the secretion of IL-6 and TNF-α by *E. coli*-derived vesicles (see Example 22).

In yet another embodiment of the present invention, the *Cupriavidus metallidurans* strains were cultured and it was evaluated whether vesicles secreted from the strains exhibited anti-cancer treatment effects. For this purpose, a cancer model was prepared by subcutaneously injecting a cancer cell line and as a result of measuring the size of cancer tissues for 20 days after orally or intraperitoneally administering vesicles derived from *Cupriavidus metallidurans* to mice from 4 days before the treatment of the cancer cell line, it was confirmed that when the vesicles were intraperitoneally and orally administered, the size of cancer tissues was decreased as compared to that of a control, and particularly, when the vesicles were orally administered, the size of cancer tissues was remarkably decreased (see Example 23).

The pharmaceutical composition of the present invention may include a pharmaceutically acceptable carrier. The pharmaceutically acceptable carrier is typically used in formulation, and includes saline, sterile water, Ringer's solution, buffered saline, cyclodextrin, a dextrose solution, a maltodextrin solution, glycerol, ethanol, liposomes, and the like, but is not limited thereto, and may further include other typical additives such as an antioxidant and a buffer, if necessary. Further, the composition may be formulated into an injectable formulation, such as an aqueous solution, a suspension, and an emulsion, a pill, a capsule, a granule, or a tablet by additionally adding a diluent, a dispersant, a surfactant, a binder, a lubricant, and the like. With regard to suitable pharmaceutically acceptable carriers and formulations, the composition may be preferably formulated according to each ingredient by using the method disclosed in the Remington's literature. The pharmaceutical composition of the present invention is not particularly limited in formulation, but may be formulated into an injection, an inhalant, an external preparation for skin, an oral ingestion, or the like.

The pharmaceutical composition of the present invention may be orally administered or may be parenterally administered (for example, administered intravenously, subcutaneously, intradermally, intranasally, or the intratracheally) according to the target method, and the administration dose may vary depending on the patient's condition and body weight, severity of disease, drug form, and administration route and period, but may be appropriately selected by those of ordinary skill in the art.

The pharmaceutical composition according to the present invention is administered in a pharmaceutically effective amount. In the present invention, the pharmaceutically effective amount refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields. The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

Specifically, the effective amount of the pharmaceutical composition according to the present invention may vary depending on the patient's age, sex, and body weight, and generally, 0.001 to 150 mg of the composition and preferably, 0.01 to 100 mg of the composition, per 1 kg of body weight, may be administered daily or every other day or may be administered once to three times a day. However, since the effective amount may be increased or decreased depending on the administration route, the severity of obesity, the gender, the body weight, the age, and the like, the administration dose is not intended to limit the scope of the present invention in any way.

In an inhalant composition of the present invention, the active ingredient may be directly added to an inhalant or may be used in combination with other ingredients, and may be appropriately used according to a general method. A mixing amount of the active ingredient may be appropriately determined according to the purpose of use thereof (for prevention or treatment).

The food composition of the present invention includes a health functional food composition. The food composition according to the present invention may be used by adding an active ingredient as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the composition of the present invention is added in an amount of 15 wt % or less, preferably 10 wt % or less based on the raw materials.

Other ingredients are not particularly limited, except that the food composition of the present invention contains the active ingredient as an essential ingredient at the indicated ratio, and the food composition of the present invention may contain various flavorants, natural carbohydrates, and the like, like a typical beverage, as an additional ingredient. Examples of the above-described natural carbohydrate include common sugars such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, and erythritol. As the flavorant other than those described above, a natural flavorant (thaumatin, stevia extract (for example, rebaudioside A, glycyrrhizin and the like), and a synthetic flavorant (saccharin, aspartame and the like) may be advantageously used. The proportion of the natural carbohydrate may be appropriately determined by the choice of those of ordinary skill in the art.

The food composition of the present invention may contain various nutrients, vitamins, minerals (electrolytes), flavoring agents such as synthetic flavoring agents and natural flavoring agents, colorants and fillers (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in a carbonated beverage, or the like, in addition to the additives. These ingredients may be used either alone or in combinations thereof. The ratio of these additives may also be appropriately selected by those of ordinary skill in the art.

Hereinafter, preferred Examples for helping the understanding of the present invention will be suggested. However, the following Examples are provided only to more easily understand the present invention, and the contents of the present invention are not limited by the following Examples.

MODES OF THE INVENTION

Examples

Example 1. Analysis of In Vivo Absorption, Distribution, and Excretion Patterns of Intestinal Bacteria and Vesicles Derived from Bacteria In order to evaluate whether intestinal bacteria and vesicles derived from bacteria were systemically absorbed through the gastrointestinal tract, an experiment was performed with the following method. A dose of 50 µg of each of intestinal bacteria and vesicles derived from intestinal bacteria labeled with fluorescence in the stomach of a mouse were administered to the gastrointestinal tract, and fluorescence was measured after 0 minute, 5 minutes, 3 hours, 6 hours, and 12 hours. As a result of observing the entire image of the mouse, as illustrated in FIG. 1A, the bacteria were not systemically absorbed, but the vesicles derived from bacteria were systemically absorbed 5 minutes after administration, and fluorescence was strongly observed in the bladder 3 hours after administration, so that it could be seen that the vesicles were excreted to the urinary tract. Further, it could be seen that the vesicles were present in the body until 12 hours after administration.

Figure 1B:
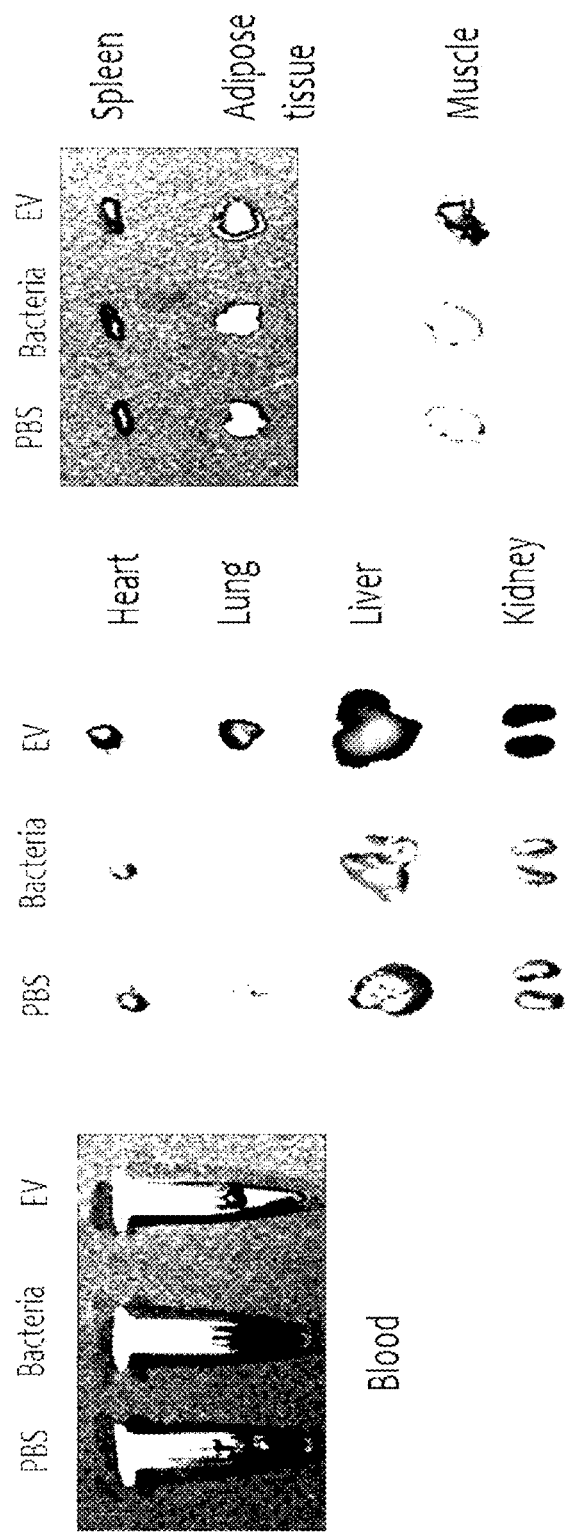
FIG. 1B is a result of evaluating the in vivo distribution patterns of the bacteria and the vesicles by harvesting blood, kidneys, liver, and various organs at 12 hours after orally administering the bacteria and the vesicles.

In addition, in order to evaluate the pattern in which the intestinal bacteria and the vesicles derived from the intestinal bacteria infiltrated into various organs after they were systemically absorbed, 50 µg of bacteria and vesicles derived from bacteria labeled with fluorescence were administered in the same manner as described above, and then the blood, heart, lungs, liver, kidneys, spleen, fat, and muscle were collected 12 hours after administration. As a result of observing fluorescence in the collected tissues, as illustrated in FIG. 1B, it could be seen that the vesicles derived from bacteria were distributed in the blood, heart, lungs, liver, spleen, fat, muscle, and kidneys but the bacteria were not absorbed.

Example 2. Metagenomic Analysis of Vesicles Derived from Bacteria in Clinical Sample A clinical sample such as blood, urine, stool or saliva was first put into a 10-ml tube, suspended matter was allowed to settle down by centrifugation (3,500×g, 10 min, 4° C.), and only the supernatant was transferred to a new 10-ml tube. After bacteria and impurities were removed by using a 0.22-µm filter, they were transferred to a Centriprep tube (centrifugal filters 50 kD) and centrifuged at 1,500×g and 4° C. for 15 minutes, materials smaller than 50 kD were discarded, and the residue was concentrated to 10 ml. After bacteria and impurities were removed once again by using a 0.22-µm filter, the supernatant was discarded by using a ultra-high speed centrifugation at 150,000×g and 4° C. for 3 hours with a Type 90Ti rotor, and an aggregated pellet was dissolved in physiological saline (PBS).

Internal DNA was extracted out of the lipid by boiling 100 µl of the vesicles isolated by the above method at 100° C., and then cooled on ice for 5 minutes. And then, in order to remove the remaining suspended matter, the DNA was centrifuged at 10,000×g and 4° C. for 30 minutes, and only the supernatant was collected. And, the amount of DNA was quantified by using Nanodrop. Thereafter, in order to confirm whether the DNA derived from bacteria was present in the extracted DNA, PCR was performed with 16s rDNA primers shown in the following Table 1 and it was confirmed that genes derived from bacteria were present in the extracted genes.

TABLE 1

| primer | | Sequence | SEQ ID No. |
|---|---|---|---|
| 16S rDNA | 16S_V3_F | 5'-TCGTCGGCAGCGTCAGATGTGTATAAGAGACAGCCTACGGGNGGCWGCAG-3' | 1 |
| | 16S_V4_R | 5'-GTCTCGTGGGCTCGGAGATGTGTATAAGAGACAGGACTACHVGGGTATCTAATCC | 2 |

The DNA extracted by the above method was amplified using the 16S rDNA primers, and then sequencing was performed (Illumina MiSeq sequencer), the results were output as a standard flowgram format (SFF) file, the SFF file was converted into a sequence file (.fasta) and a nucleotide quality score file using GS FLX software (v2.9), and then the reliability estimation for the reads was confirmed, and a portion in which the window (20 bps) average base call accuracy was less than 99% (Phred score<20) was removed. For the operational taxonomy unit (OTU) analysis, clustering was performed according to sequence similarity by using UCLUST and USEARCH, the genus, family, order, class, and phylum were clustered based on 94%, 90%, 85%, 80%, and 75% sequence similarity, respectively, classification was performed at the phylum, class, order, family, and genus levels of each OUT, and bacteria having a sequence similarity of 97% or more at the genus level were profiled by using the 16S RNA sequence database (108,453 sequences) of BLASTN and GreenGenes (QIIME).

Figure 2A:
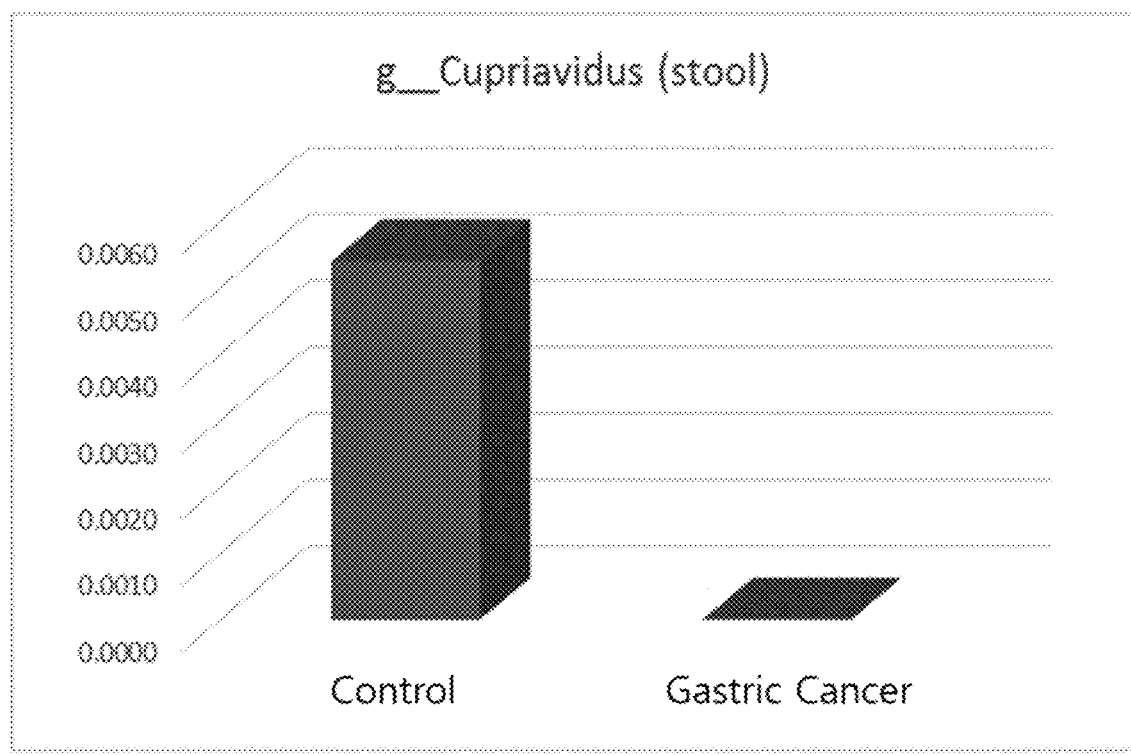

Example 3. Metagenomic Analysis of Vesicles Derived from Bacteria in Stool, Blood, and Urine of Patient with Gastric Cancer Genes were extracted from vesicles present in stool samples of 63 gastric cancer patients and 126 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the stool from the patients with gastric cancer as compared to the stool from the normal individuals (see Table 2 and FIG. 2A).

TABLE 2

| Stool | Control | | Gastric cancer | | t-test | |
|---|---|---|---|---|---|---|
| Taxon | Mean | SD | Mean | SD | p-value | Ratio |
| g_*Cupriavidus* | 0.0054 | 0.0308 | 0.0000 | 0.0001 | 0.001 | 0.01 |

Figure 2B:
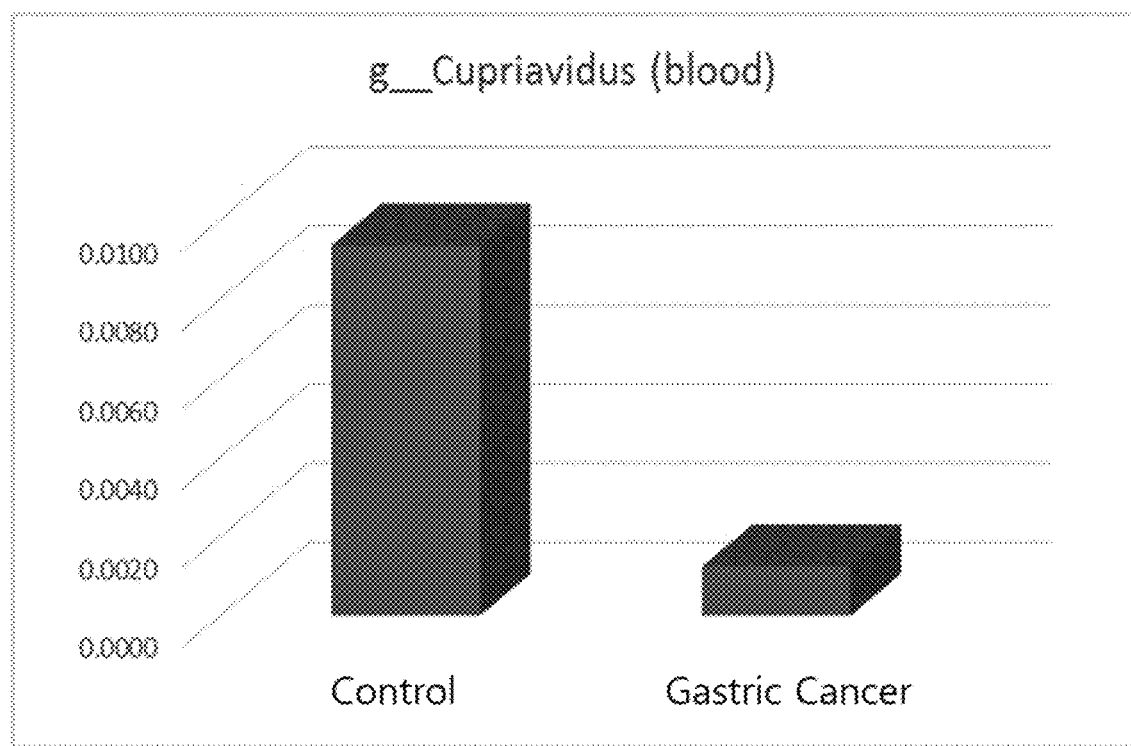

Genes were extracted from vesicles present in blood samples of 67 gastric cancer patients and 198 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the blood from the patients with gastric cancer as compared to the blood from the normal individuals (see Table 3 and FIG. 2B).

TABLE 3

| Blood | Control | | Gastric cancer | | t-test | |
|---|---|---|---|---|---|---|
| Taxon | Mean | SD | Mean | SD | p-value | Ratio |
| g_*Cupriavidus* | 0.0094 | 0.0158 | 0.0013 | 0.0026 | <0.0001 | 0.13 |

Figure 2C:
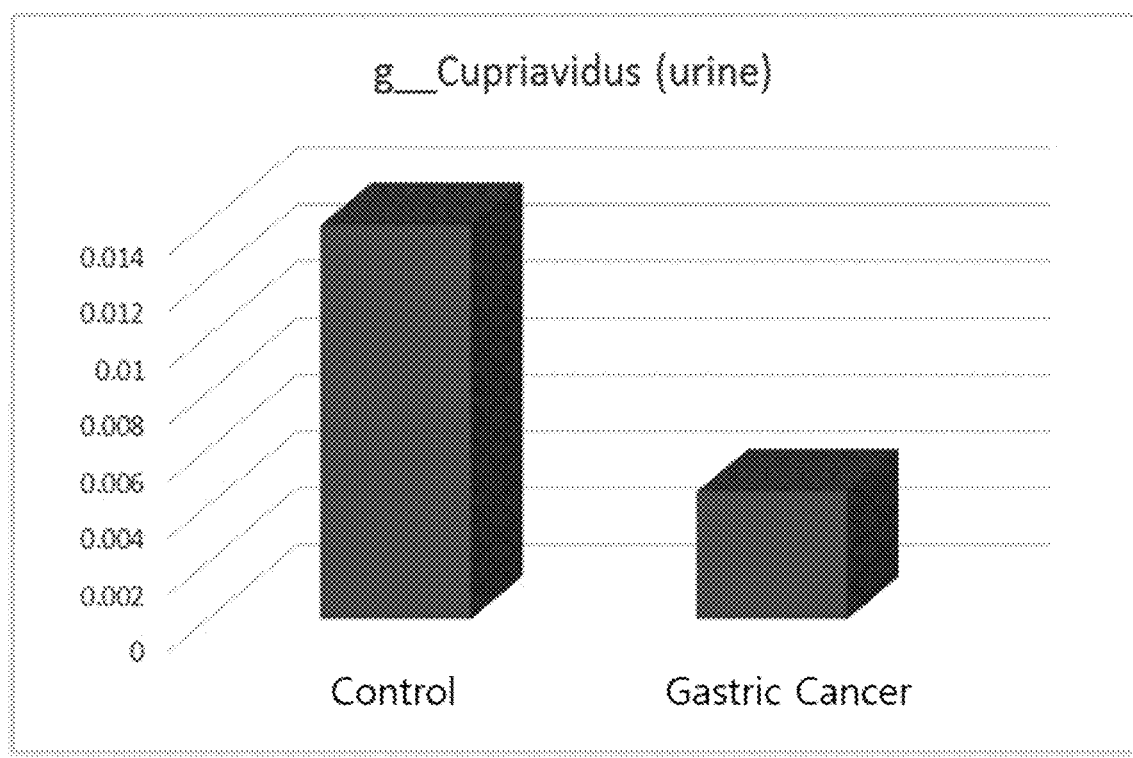

Further, genes were extracted from vesicles present in urine samples of 61 gastric cancer patients and 120 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the urine from the patients with gastric cancer as compared to the urine from the normal individuals (see Table 4 and FIG. 2C).

TABLE 4

| Urine | Control | | Gastric cancer | | t-test | |
|---|---|---|---|---|---|---|
| Taxon | Mean | SD | Mean | SD | p-value | Ratio |
| g__*Cupriavidus* | 0.0139 | 0.0687 | 0.0045 | 0.0071 | 0.01 | 0.33 |

Figure 3A:
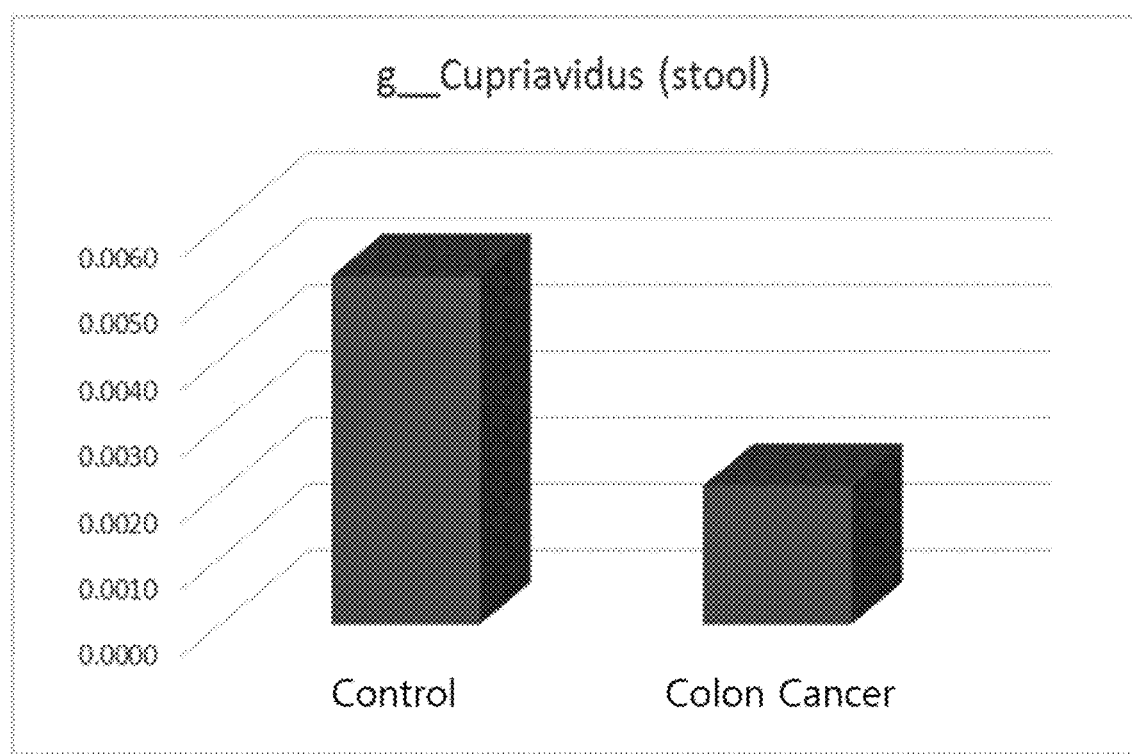

Example 4. Metagenomic Analysis of Vesicles Derived from Bacteria in Stool and Urine of Patient with Colon Cancer Genes were extracted from vesicles present in stool samples of 52 colon cancer patients and 83 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the stool from the patients with colon cancer as compared to the stool from the normal individuals (see Table 5 and FIG. 3A).

TABLE 5

| Stool | Control | | Colon cancer | | t-test | |
|---|---|---|---|---|---|---|
| Taxon | Mean | SD | Mean | SD | p-value | Ratio |
| g__*Cupriavidus* | 0.0052 | 0.0306 | 0.0021 | 0.0082 | 0.01 | 0.40 |

Figure 3B:
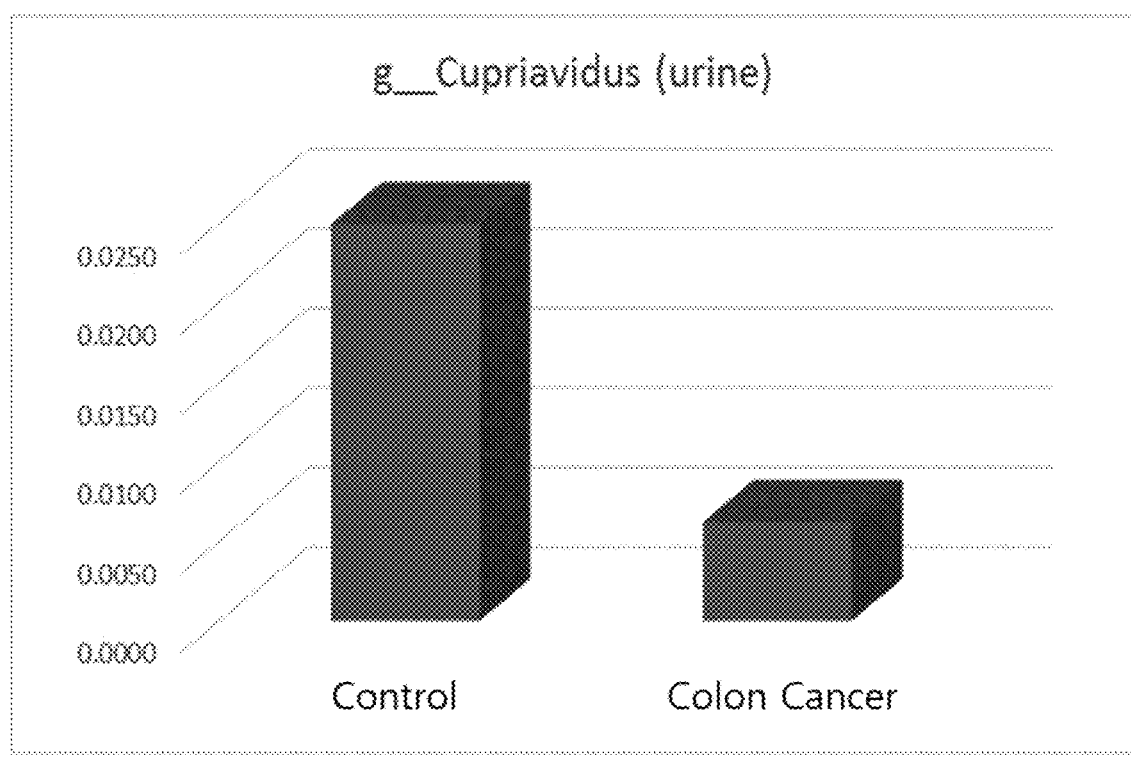

Further, genes were extracted from vesicles present in urine samples of 38 colon cancer patients and 38 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the urine from the patients with colon cancer as compared to the urine from the normal individuals (see Table 6 and FIG. 3B).

TABLE 6

| Urine | Control | | Colon cancer | | t-test | |
|---|---|---|---|---|---|---|
| Taxon | Mean | SD | Mean | SD | p-value | Ratio |
| g__*Cupriavidus* | 0.0249 | 0.1064 | 0.0062 | 0.0039 | 0.04 | 0.25 |

Figure 4:
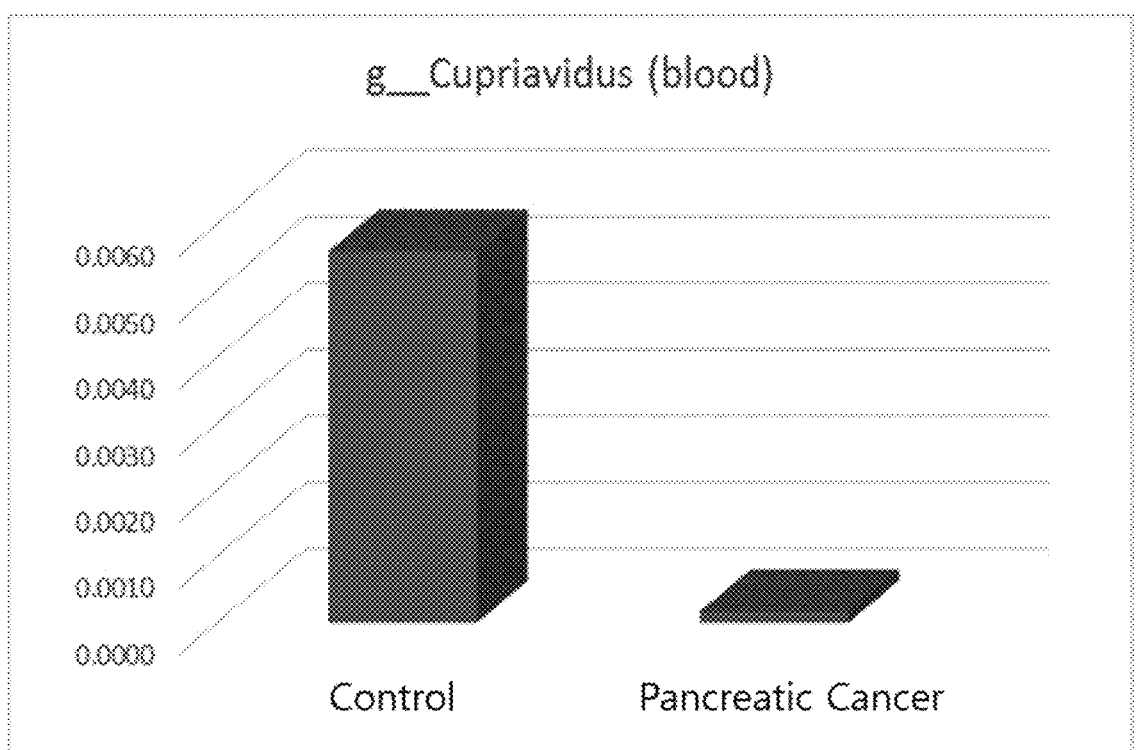
FIG. 4 is a result of comparing the distributions of vesicles derived from bacteria belonging to the genus *Cupriavidus* after metagenomic analysis of bacteria-derived vesicles present in the blood of pancreatic cancer patients and a normal individuals.

Example 5. Metagenomic Analysis of Vesicles Derived from Bacteria in Blood of Patient with Pancreatic Cancer Genes were extracted from vesicles present in blood samples of 291 pancreatic cancer patients and 291 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the blood from the patients with pancreatic cancer as compared to the blood from the normal individuals (see Table 7 and FIG. 4).

TABLE 7

| Blood | Control | | Pancreatic cancer | | t-test | |
|---|---|---|---|---|---|---|
| Taxon | Mean | SD | Mean | SD | p-value | Ratio |
| g__*Cupriavidus* | 0.0056 | 0.0132 | 0.0002 | 0.0010 | <0.0001 | 0.03 |

Figure 5:
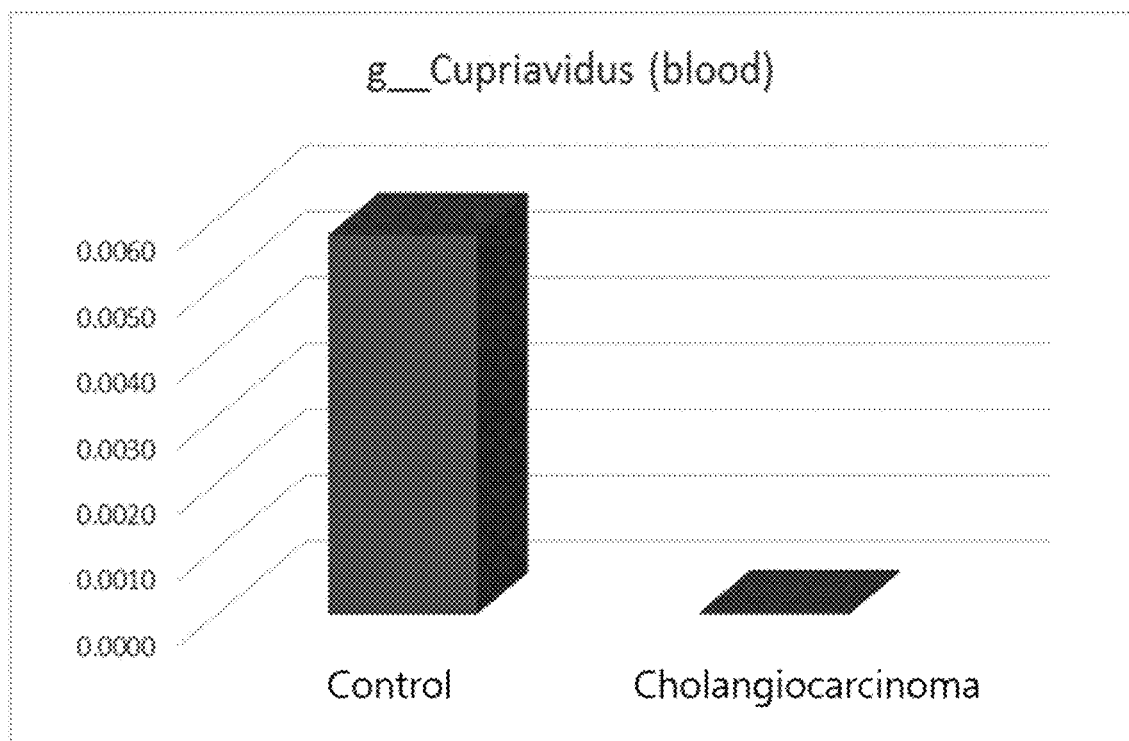
FIG. 5 is a result of comparing the distributions of vesicles derived from bacteria belonging to the genus *Cupriavidus* after metagenomic analysis of bacteria-derived vesicles present in the blood of cholangiocarcinoma patients and a normal individuals.

Example 6. Metagenomic Analysis of Vesicles Derived from Bacteria in Blood of Patient with Cholangiocarcinoma Genes were extracted from vesicles present in blood samples of 79 cholangiocarcinoma patients and 259 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the blood from the patients with cholangiocarcinoma as compared to the blood from the normal individuals (see Table 8 and FIG. 5).

TABLE 8

| Blood | Control | | Cholangiocarcinoma | | t-test | |
|---|---|---|---|---|---|---|
| Taxon | Mean | SD | Mean | SD | p-value | Ratio |
| g__*Cupriavidus* | 0.0058 | 0.0135 | 0.0000 | 0.0002 | <0.0001 | 0.01 |

Figure 6A:
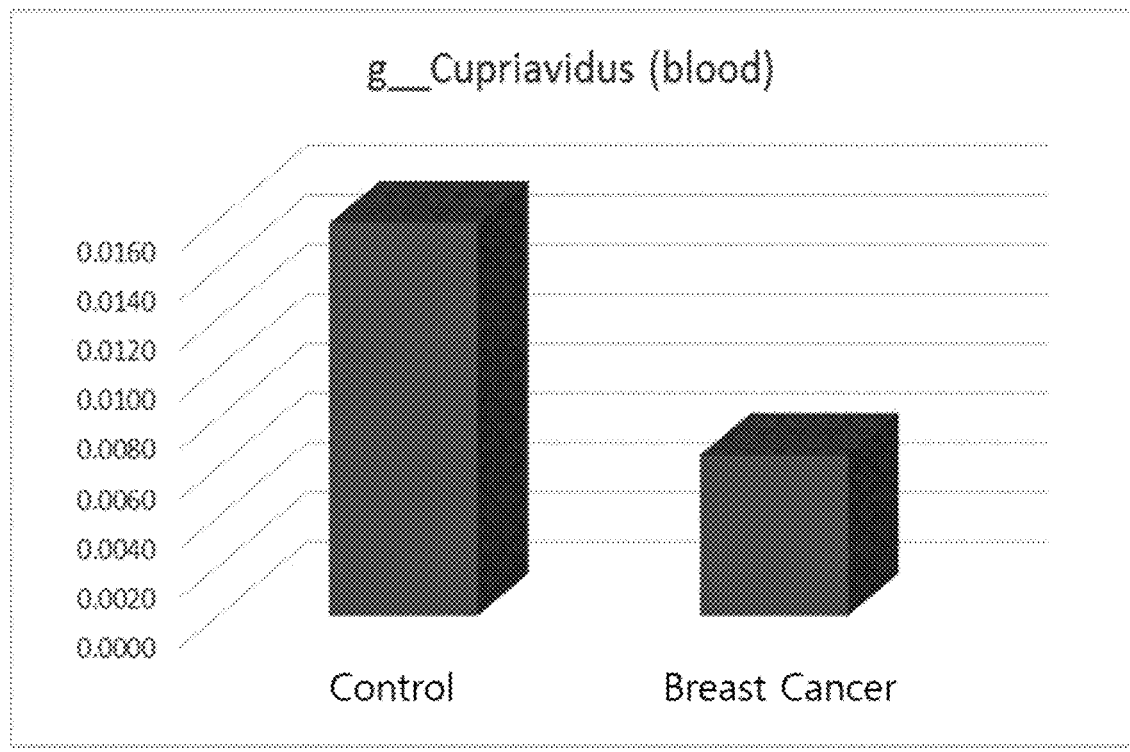

Example 7. Metagenomic Analysis of Vesicles Derived from Bacteria in Blood and Urine of Patient with Breast Cancer Genes were extracted from vesicles present in blood samples of 96 breast cancer patients and 192 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the blood from the patients with breast cancer as compared to the blood from the normal individuals (see Table 9 and FIG. 6A).

TABLE 9

| Blood | Control | | Breast cancer | | t-test | |
|---|---|---|---|---|---|---|
| Taxon | Mean | SD | Mean | SD | p-value | Ratio |
| g__*Cupriavidus* | 0.0158 | 0.0347 | 0.0065 | 0.0059 | 0.0004 | 0.41 |

Figure 6B:
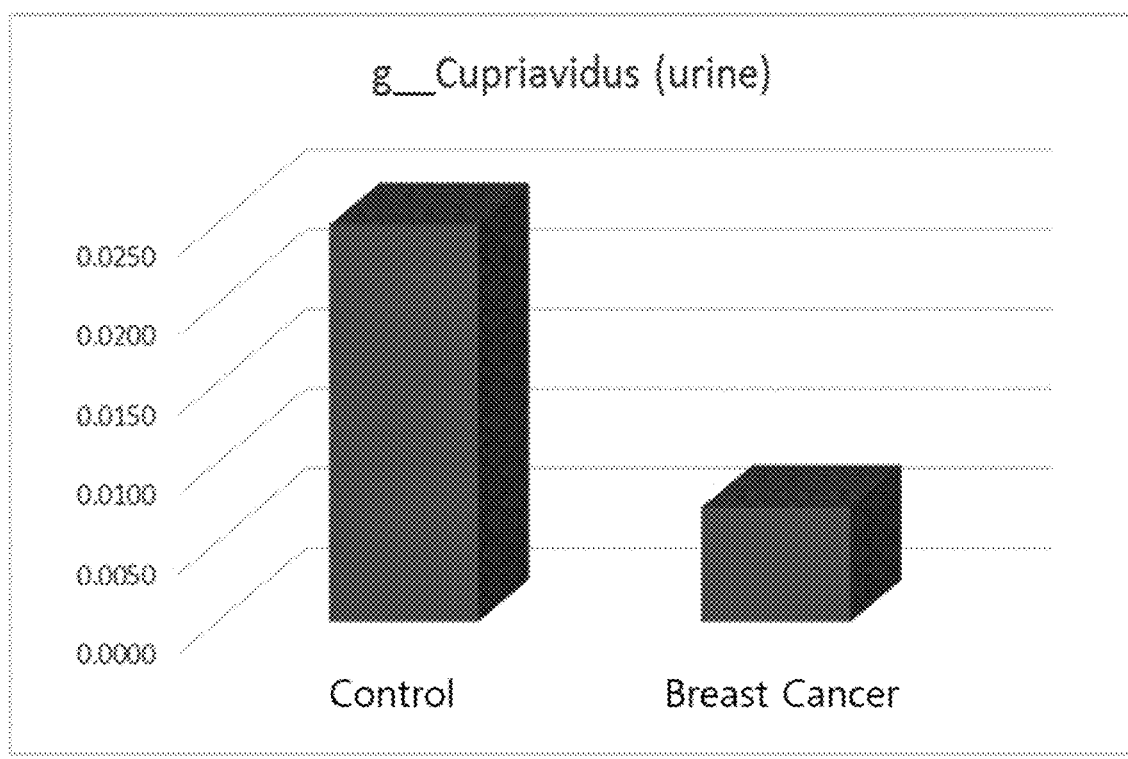

Genes were extracted from vesicles present in urine samples of 127 breast cancer patients and 220 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the urine from the patients with breast cancer as compared to the urine from the normal individuals (see Table 10 and FIG. 6B).

TABLE 10

| Urine | Control | | Breast cancer | | t-test | |
|---|---|---|---|---|---|---|
| Taxon | Mean | SD | Mean | SD | p-value | Ratio |
| g__*Cupriavidus* | 0.0249 | 0.0865 | 0.0072 | 0.0065 | 0.002 | 0.29 |

Figure 7A:
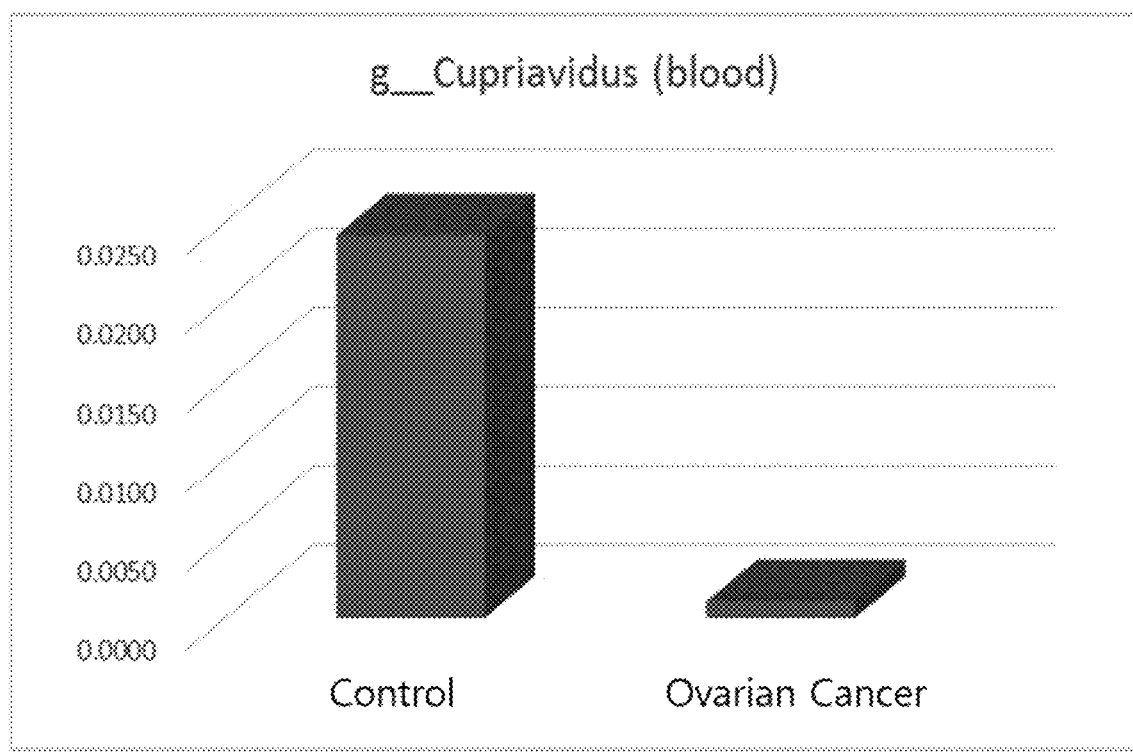

Example 8. Metagenomic Analysis of Vesicles Derived from Bacteria in Blood and Urine of Patient with Ovarian Cancer Genes were extracted from vesicles present in blood samples of 136 ovarian cancer patients and 136 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the blood from the patients with ovarian cancer as compared to the blood from the normal individuals (see Table 11 and FIG. 7A).

TABLE 11

| Blood | Control | | Ovarian cancer | | t-test | |
|---|---|---|---|---|---|---|
| Taxon | Mean | SD | Mean | SD | p-value | Ratio |
| g__*Cupriavidus* | 0.0242 | 0.0432 | 0.0011 | 0.0017 | <0.0001 | 0.04 |

Figure 7B:
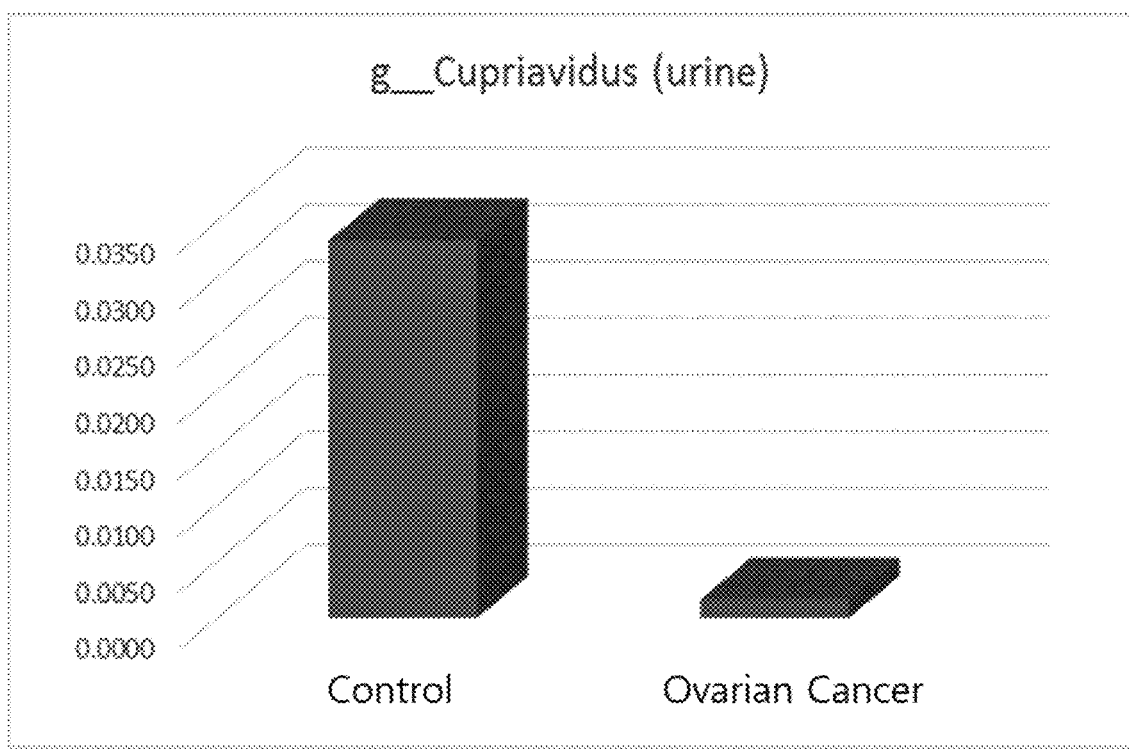

Genes were extracted from vesicles present in urine samples of 136 ovarian cancer patients and 136 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the urine from the patients with ovarian cancer as compared to the urine from the normal individuals (see Table 12 and FIG. 7B).

TABLE 12

| Urine | Control | | Ovarian cancer | | t-test | |
|---|---|---|---|---|---|---|
| Taxon | Mean | SD | Mean | SD | p-value | Ratio |
| g__*Cupriavidus* | 0.0333 | 0.0988 | 0.0016 | 0.0028 | 0.0002 | 0.05 |

Figure 8A:
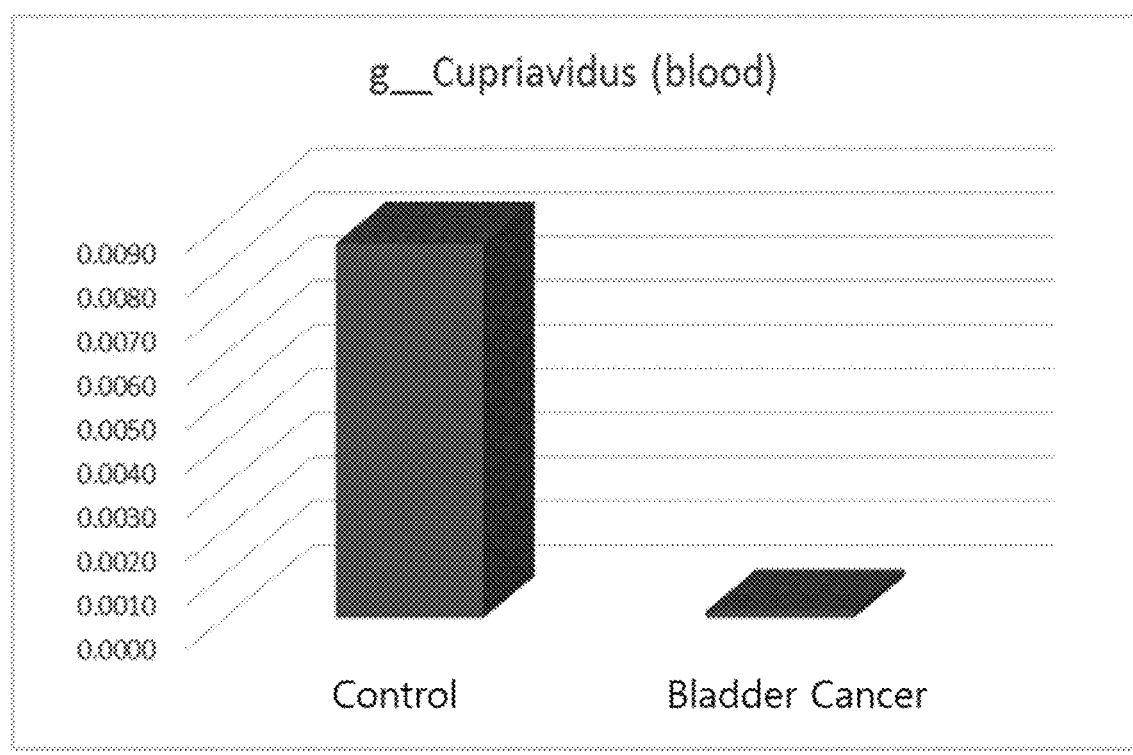

Example 9. Metagenomic Analysis of Vesicles Derived from Bacteria in Blood and Urine of Patient with Bladder Cancer Genes were extracted from vesicles present in blood samples of 96 bladder cancer patients and 184 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the blood from the patients with bladder cancer as compared to the blood from the normal individuals (see Table 13 and FIG. 8A).

TABLE 13

| Blood | Control | | Bladder cancer | | t-test | |
|---|---|---|---|---|---|---|
| Taxon | Mean | SD | Mean | SD | p-value | Ratio |
| g__*Cupriavidus* | 0.0085 | 0.0202 | 0.0002 | 0.0002 | <0.0001 | 0.02 |

Figure 8B:
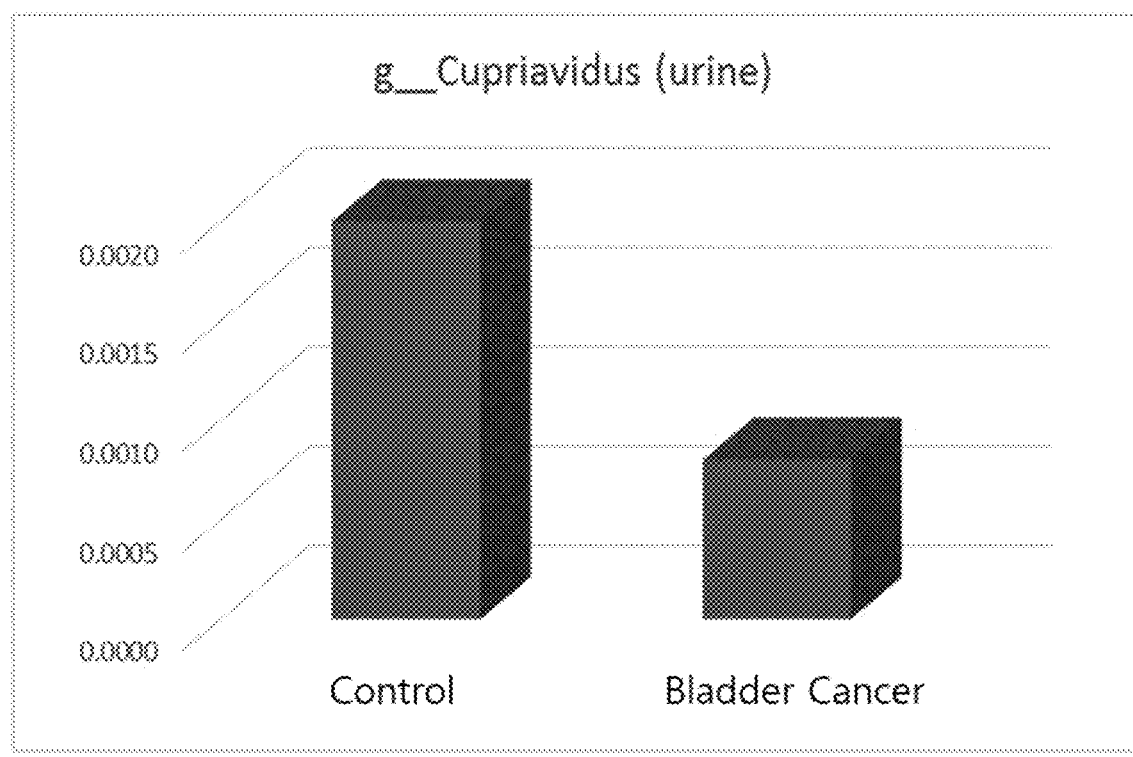

Further, Genes were extracted from vesicles present in urine samples of 95 bladder cancer patients and 157 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the urine from the patients with bladder cancer as compared to the urine from the normal individuals (see Table 14 and FIG. 8B).

TABLE 14

| Urine | Control | | Bladder cancer | | t-test | |
|---|---|---|---|---|---|---|
| Taxon | Mean | SD | Mean | SD | p-value | Ratio |
| g__*Cupriavidus* | 0.0020 | 0.0039 | 0.0008 | 0.0013 | 0.008 | 0.42 |

Figure 9:
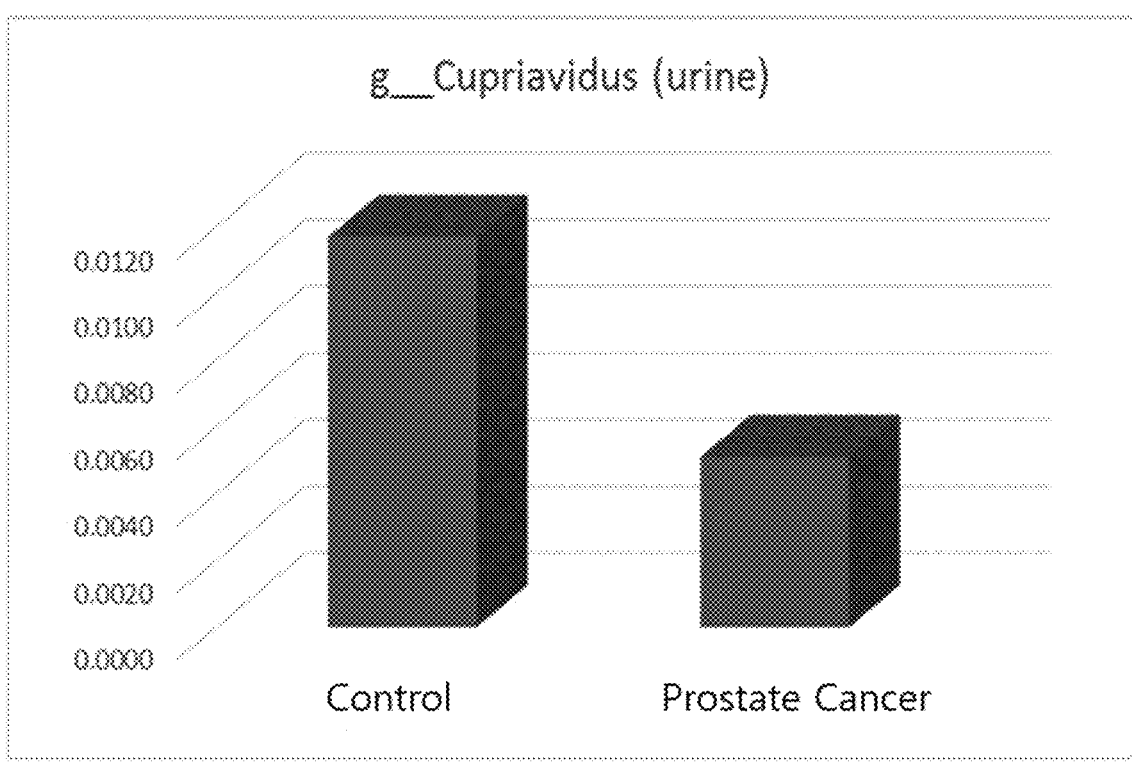
FIG. 9 is a result of comparing the distributions of vesicles derived from bacteria belonging to the genus *Cupriavidus* after metagenomic analysis of bacteria-derived vesicles present in the urine of prostate cancer patients and a normal individuals.

Example 10. Metagenomic Analysis of Vesicles Derived from Bacteria in Urine of Patient with Prostate Cancer Genes were extracted from vesicles present in urine samples of 53 prostate cancer patients and 159 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the urine from the patients with prostate cancer as compared to the urine from the normal individuals (see Table 15 and FIG. 9).

TABLE 15

| Urine | Control | | Prostate cancer | | t-test | |
|---|---|---|---|---|---|---|
| Taxon | Mean | SD | Mean | SD | p-value | Ratio |
| g__*Cupriavidus* | 0.0117 | 0.0530 | 0.0051 | 0.0054 | 0.01 | 0.44 |

Figure 10:
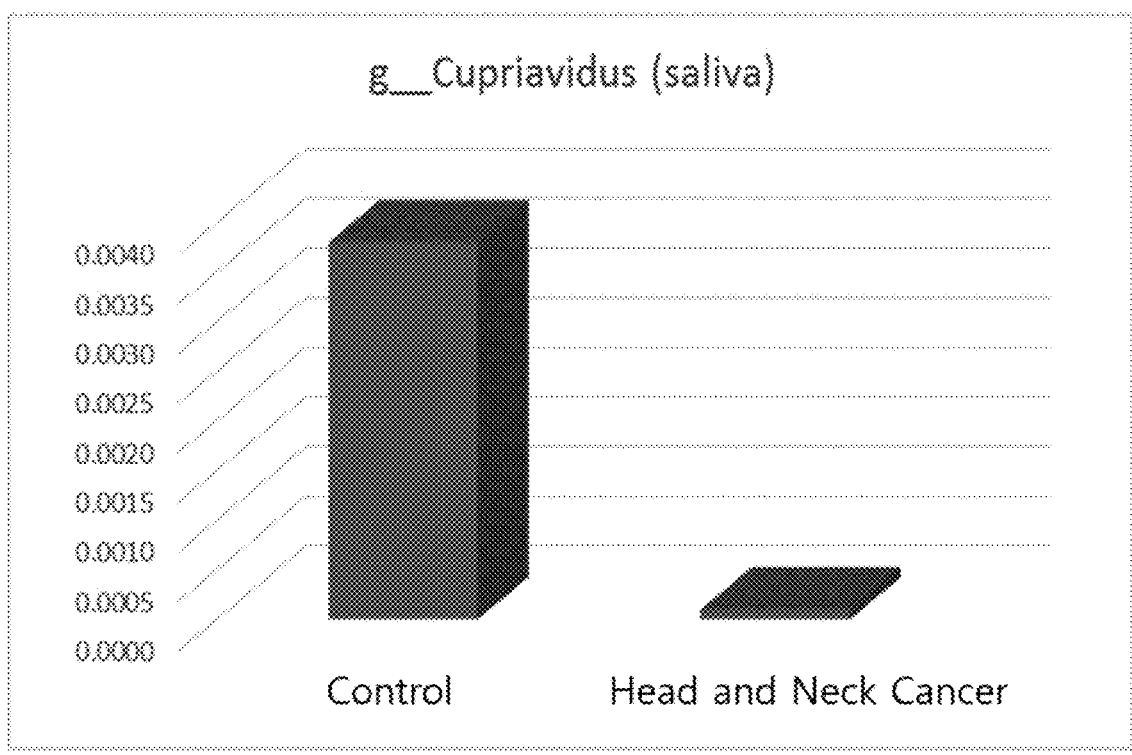
FIG. 10 is a result of comparing the distributions of vesicles derived from bacteria belonging to the genus *Cupriavidus* after metagenomic analysis of bacteria-derived vesicles present in the saliva of head and neck cancer patients and a normal individuals.

Example 11. Metagenomic Analysis of Vesicles Derived from Bacteria in Saliva of Patient with Head and Neck Cancer Genes were extracted from vesicles present in saliva samples of 57 head and neck cancer patients and 277 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the saliva from the patients with head and neck cancer as compared to the saliva from the normal individuals (see Table 16 and FIG. 10).

TABLE 16

| Saliva | Control | | Head and Neck Cancer | | t-test | |
|---|---|---|---|---|---|---|
| Taxon | Mean | SD | Mean | SD | p-value | Ratio |
| g_Cupriavidus | 0.0038 | 0.0105 | 0.0001 | 0.0003 | <0.0001 | 0.02 |

Figure 11:
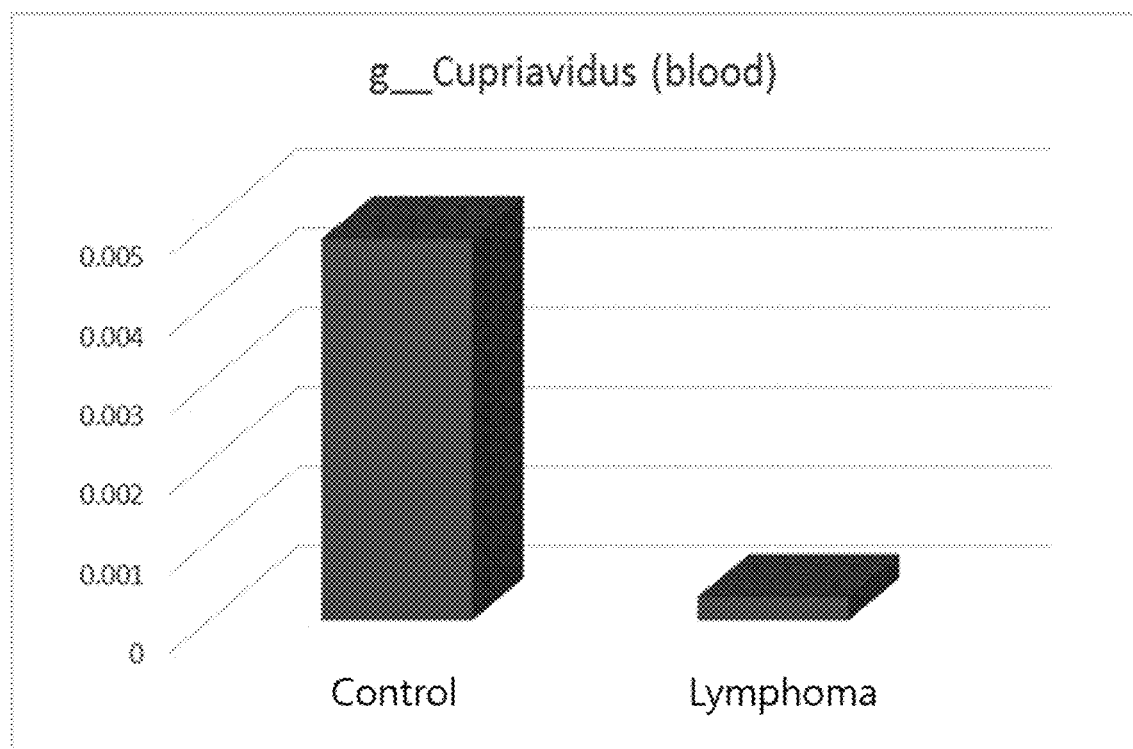
FIG. 11 is a result of comparing the distributions of vesicles derived from bacteria belonging to the genus *Cupriavidus* after metagenomic analysis of bacteria-derived vesicles present in the blood of lymphoma patients and a normal individuals.

Example 12. Metagenomic Analysis of Vesicles Derived from Bacteria in Blood of Patient with Lymphoma Genes were extracted from vesicles present in blood samples of 57 lymphoma patients and 163 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the blood from the patients with lymphoma as compared to the blood from the normal individuals (see Table 17 and FIG. 11).

TABLE 17

| Blood | Control | | Lymphoma | | t-test | |
|---|---|---|---|---|---|---|
| Taxon | Mean | SD | Mean | SD | p-value | Ratio |
| g_Cupriavidus | 0.0048 | 0.0105 | 0.0003 | 0.0011 | 0.003 | 0.05 |

Figure 12A:
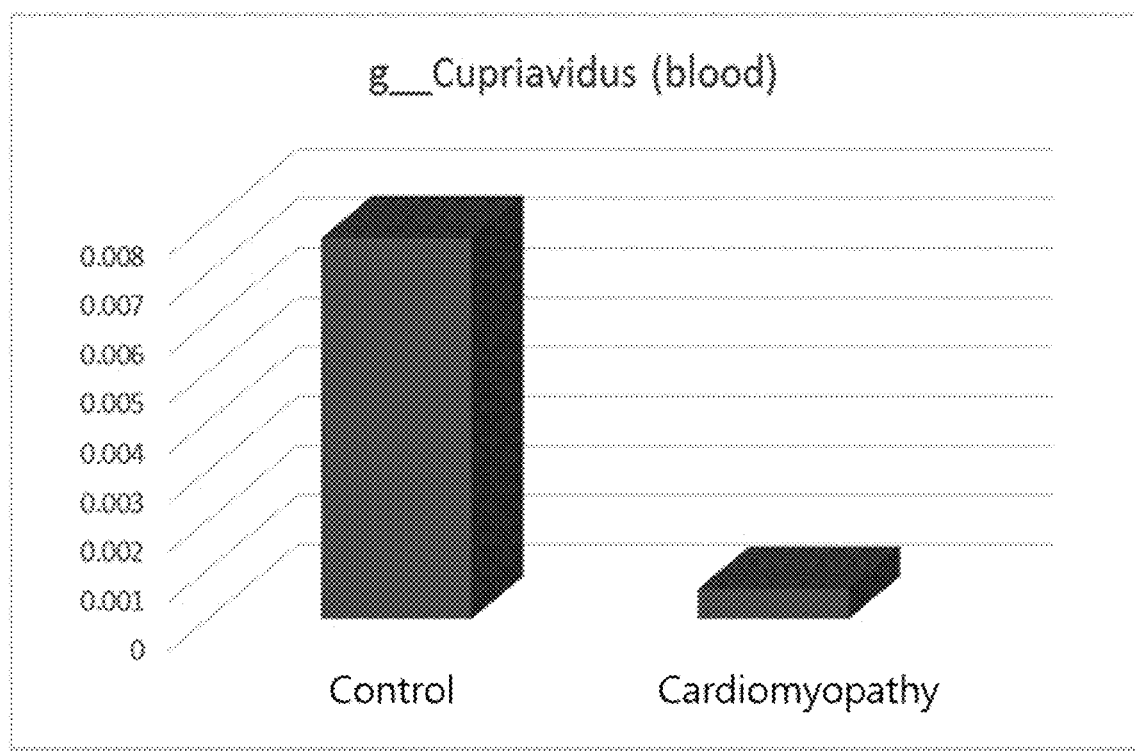

Example 13. Metagenomic Analysis of Vesicles Derived from Bacteria in Blood of Patient with Heart Diseases Genes were extracted from vesicles present in blood samples of 72 cardiomyopathy patients and 163 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the blood from the patients with cardiomyopathy as compared to the blood from the normal individuals (see Table 18 and FIG. 12A).

TABLE 18

| Blood | Control | | Cardiomyopathy | | t-test | |
|---|---|---|---|---|---|---|
| Taxon | Mean | SD | Mean | SD | p-value | Ratio |
| g_Cupriavidus | 0.0077 | 0.012 | 0.0006 | 0.0011 | 0.0002 | 0.07 |

Figure 12B:
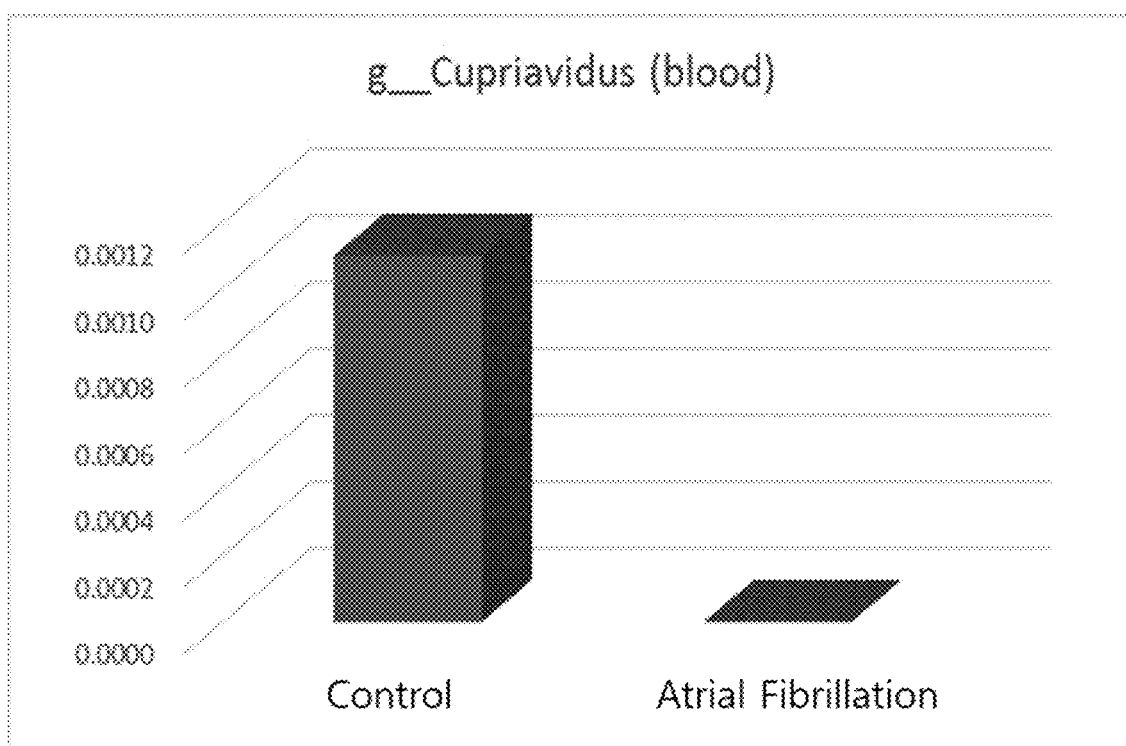

Genes were extracted from vesicles present in blood samples of 34 atrial fibrillation patients and 63 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the blood from the patients with atrial fibrillation as compared to the blood from the normal individuals (see Table 19 and FIG. 12B).

TABLE 19

| Blood | Control | | Atrial Fibrillation | | t-test | |
|---|---|---|---|---|---|---|
| Taxon | Mean | SD | Mean | SD | p-value | Ratio |
| g_Cupriavidus | 0.0011 | 0.0027 | 0.0000 | 0.0000 | 0.01 | 0.00 |

Figure 12C:
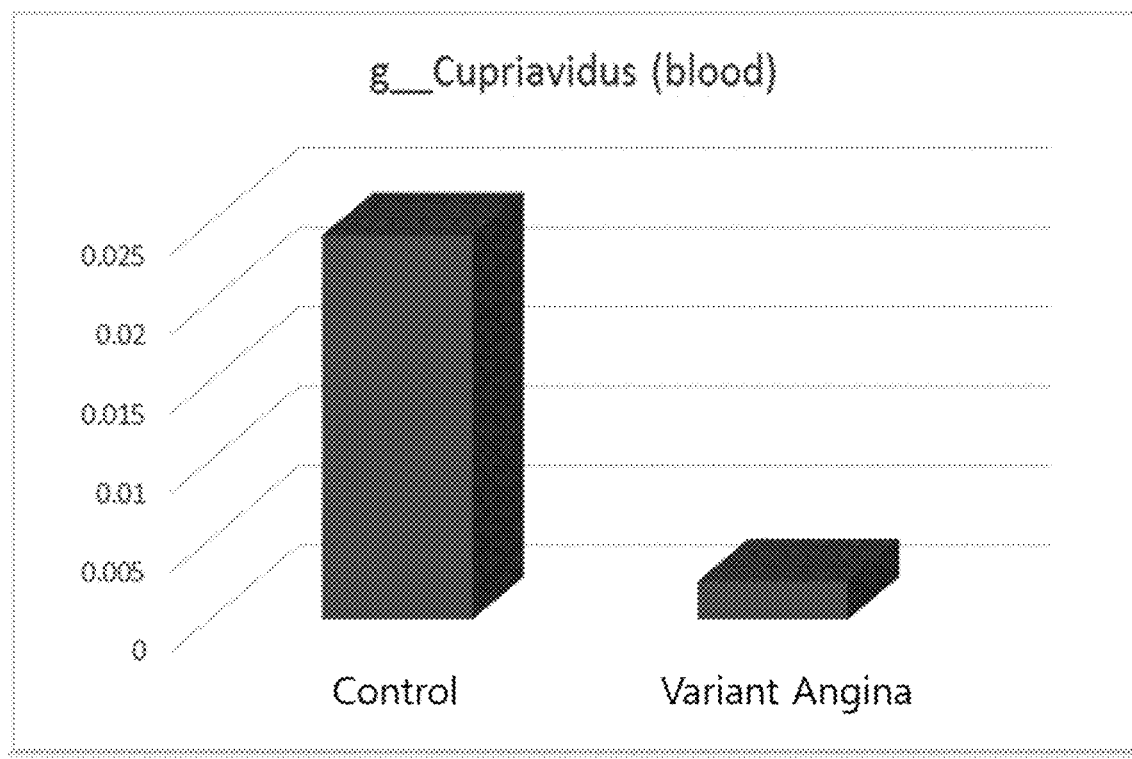

Genes were extracted from vesicles present in blood samples of 80 variant angina patients and 80 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the blood from the patients with variant angina as compared to the blood from the normal individuals (see Table 20 and FIG. 12C).

TABLE 20

| Blood | Control | | Variant Angina | | t-test | |
|---|---|---|---|---|---|---|
| Taxon | Mean | SD | Mean | SD | p-value | Ratio |
| g_Cupriavidus | 0.0242 | 0.0492 | 0.0024 | 0.004 | 0.0002 | 0.10 |

Figure 13:
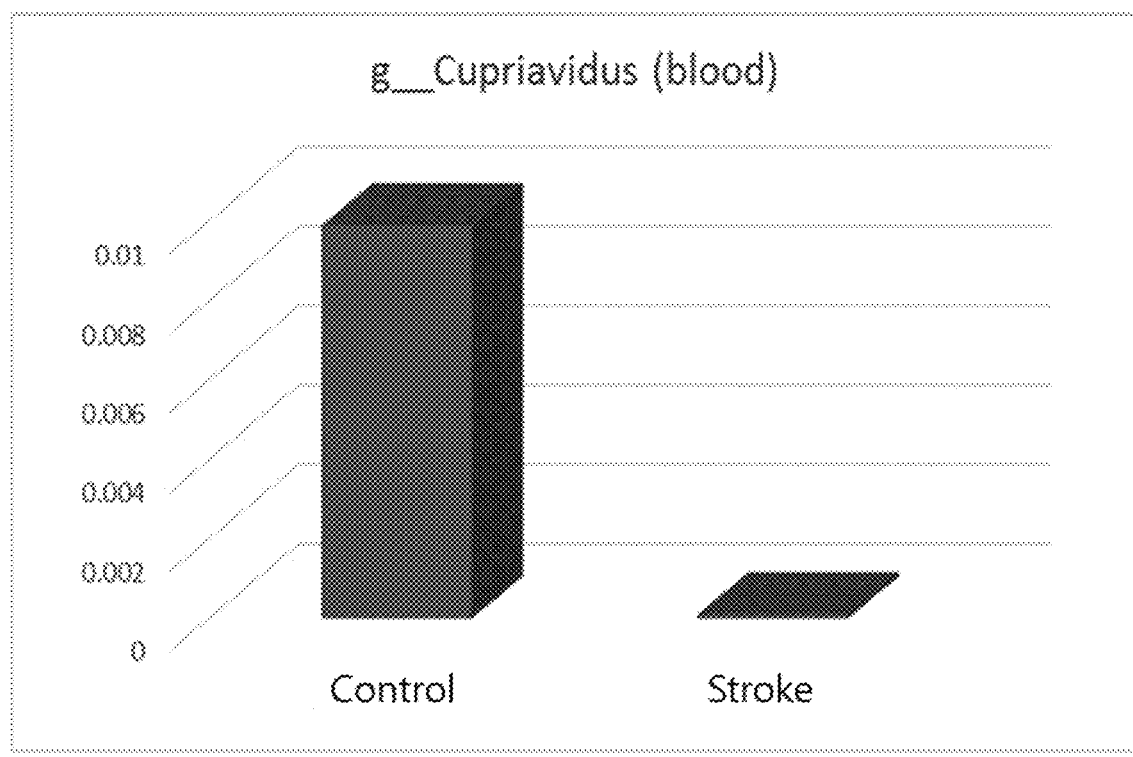
FIG. 13 is a result of comparing the distributions of vesicles derived from bacteria belonging to the genus *Cupriavidus* after metagenomic analysis of bacteria-derived vesicles present in the blood of stroke patients and a normal individuals.

Example 14. Metagenomic Analysis of Vesicles Derived from Bacteria in Blood of Patient with Stroke Genes were extracted from vesicles present in blood samples of 115 stroke patients and 109 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the blood from the patients with stroke as compared to the blood from the normal individuals (see Table 21 and FIG. 13).

TABLE 21

| Blood | Control | | Stroke | | t-test | |
|---|---|---|---|---|---|---|
| Taxon | Mean | SD | Mean | SD | p-value | Ratio |
| g_Cupriavidus | 0.0099 | 0.031 | 0.0001 | 0.0006 | 0.001 | 0.01 |

Example 15. Metagenomic Analysis of Vesicles Derived from Bacteria in Blood of Patient with Chronic Obstructive Pulmonary Disease (COPD)

Figure 14:
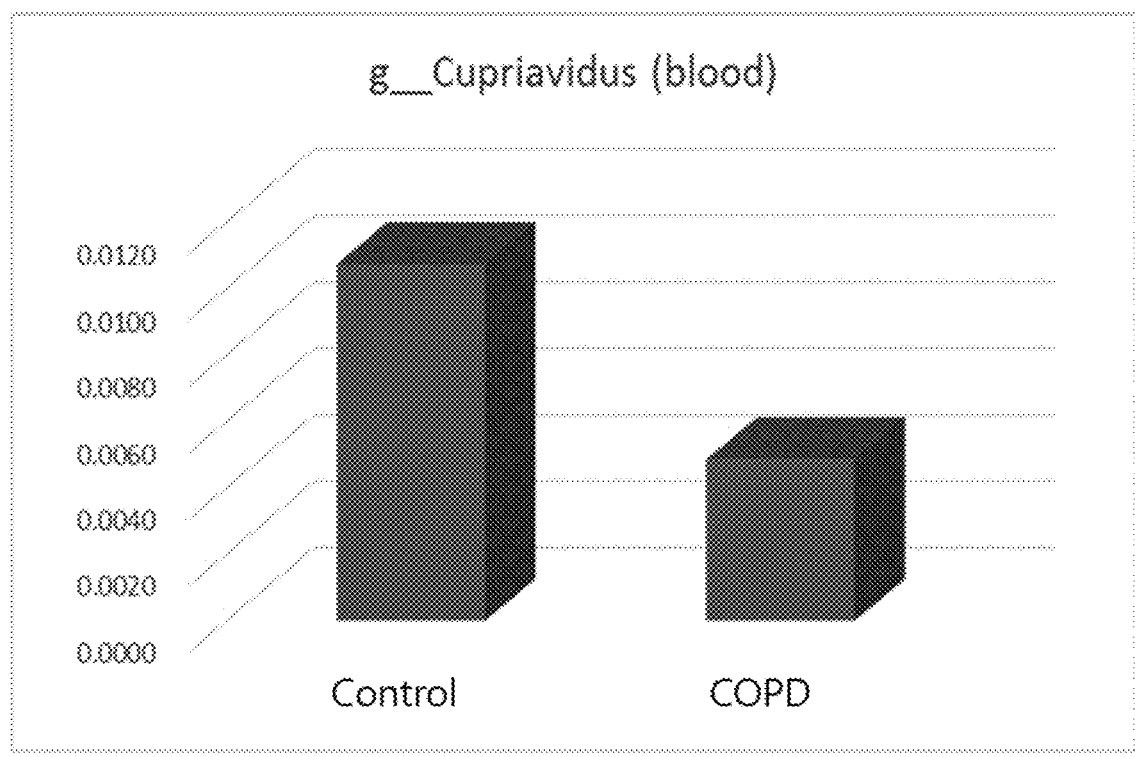
FIG. 14 is a result of comparing the distributions of vesicles derived from bacteria belonging to the genus *Cupriavidus* after metagenomic analysis of bacteria-derived vesicles present in the blood of chronic obstructive pulmonary disease patients and a normal individuals.

Genes were extracted from vesicles present in blood samples of 205 COPD patients and 231 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the blood from the patients with COPD as compared to the blood from the normal individuals (see Table 22 and FIG. 14).

TABLE 22

| Blood | Control | | COPD | | t-test | |
|---|---|---|---|---|---|---|
| Taxon | Mean | SD | Mean | SD | p-value | Ratio |
| g_*Cupriavidus* | 0.0107 | 0.0237 | 0.0049 | 0.0052 | <0.0001 | 0.45 |

Figure 15A:
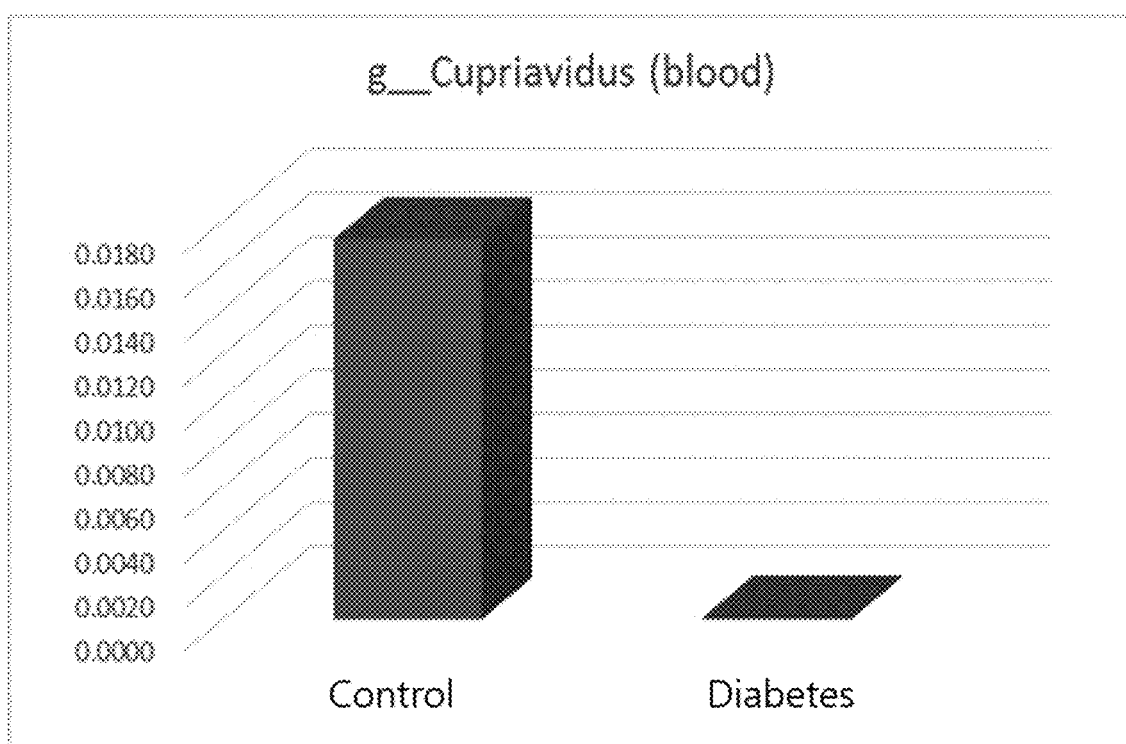

Example 16. Metagenomic Analysis of Vesicles Derived from Bacteria in Blood, Urine, and Saliva of Patient with Diabetes Genes were extracted from vesicles present in blood samples of 61 diabetes patients and 122 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the blood from the patients with diabetes as compared to the blood from the normal individuals (see Table 23 and FIG. 15A).

TABLE 23

| Blood | Control | | Diabetes | | t-test | |
|---|---|---|---|---|---|---|
| Taxon | Mean | SD | Mean | SD | p-value | Ratio |
| g_*Cupriavidus* | 0.0172 | 0.0367 | 0.0001 | 0.0001 | <0.0001 | 0.01 |

Figure 15B:
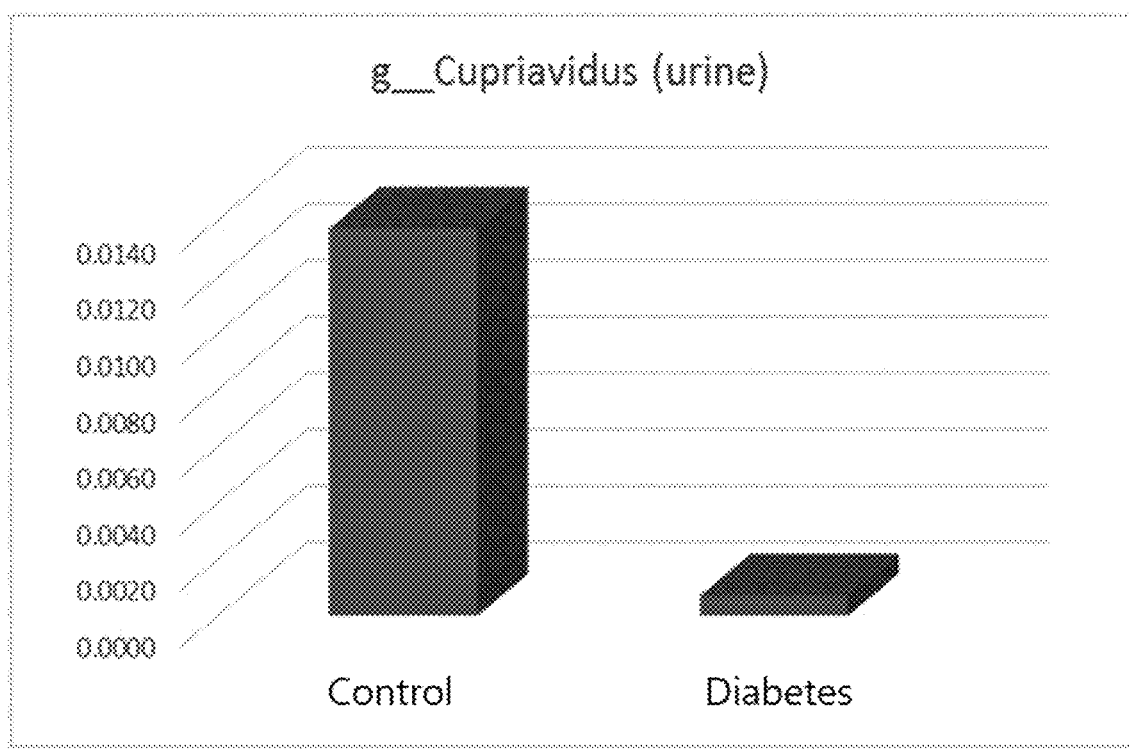

Genes were extracted from vesicles present in urine samples of 60 diabetes patients and 134 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the urine from the patients with diabetes as compared to the urine from the normal individuals (see Table 24 and FIG. 15B).

TABLE 24

| Urine | Control | | Diabetes | | t-test | |
|---|---|---|---|---|---|---|
| Taxon | Mean | SD | Mean | SD | p-value | Ratio |
| g_*Cupriavidus* | 0.0137 | 0.0551 | 0.0007 | 0.0007 | 0.007 | 0.05 |

Figure 15C:
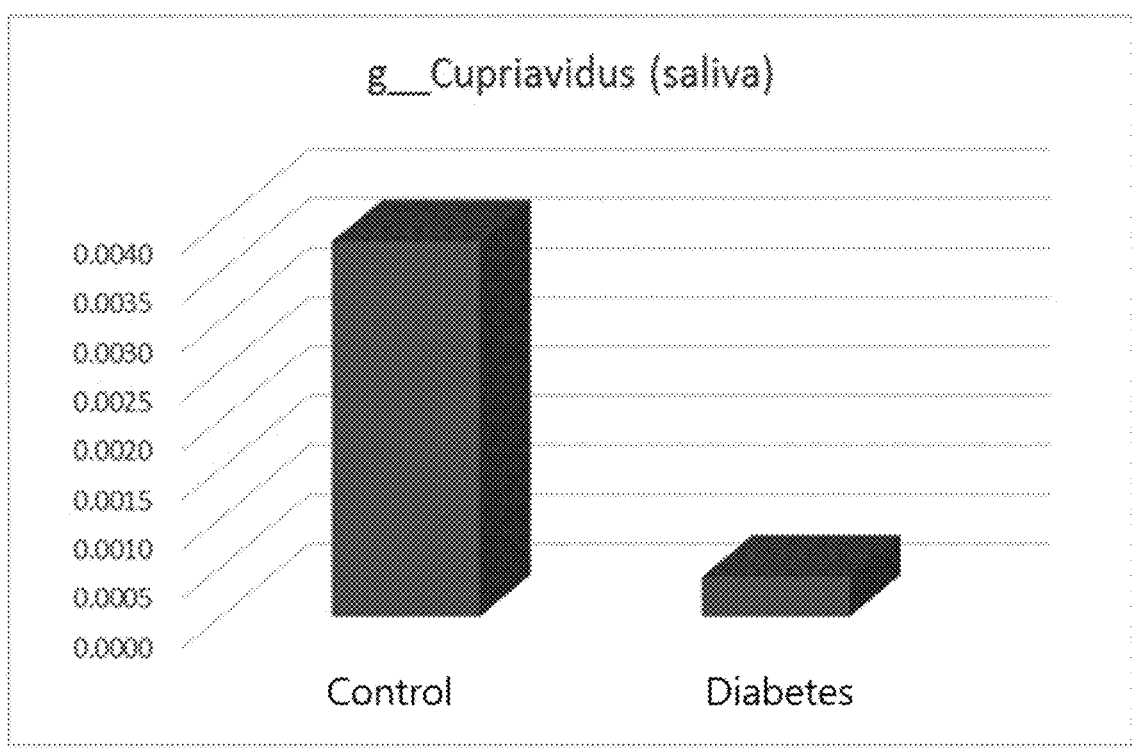

Genes were extracted from vesicles present in saliva samples of 37 diabetes patients and 277 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the saliva from the patients with diabetes as compared to the saliva from the normal individuals (see Table 25 and FIG. 15C).

TABLE 25

| Saliva | Control | | Diabetes | | t-test | |
|---|---|---|---|---|---|---|
| Taxon | Mean | SD | Mean | SD | p-value | Ratio |
| g_*Cupriavidus* | 0.0038 | 0.0105 | 0.0004 | 0.0010 | <0.0001 | 0.12 |

Figure 16:
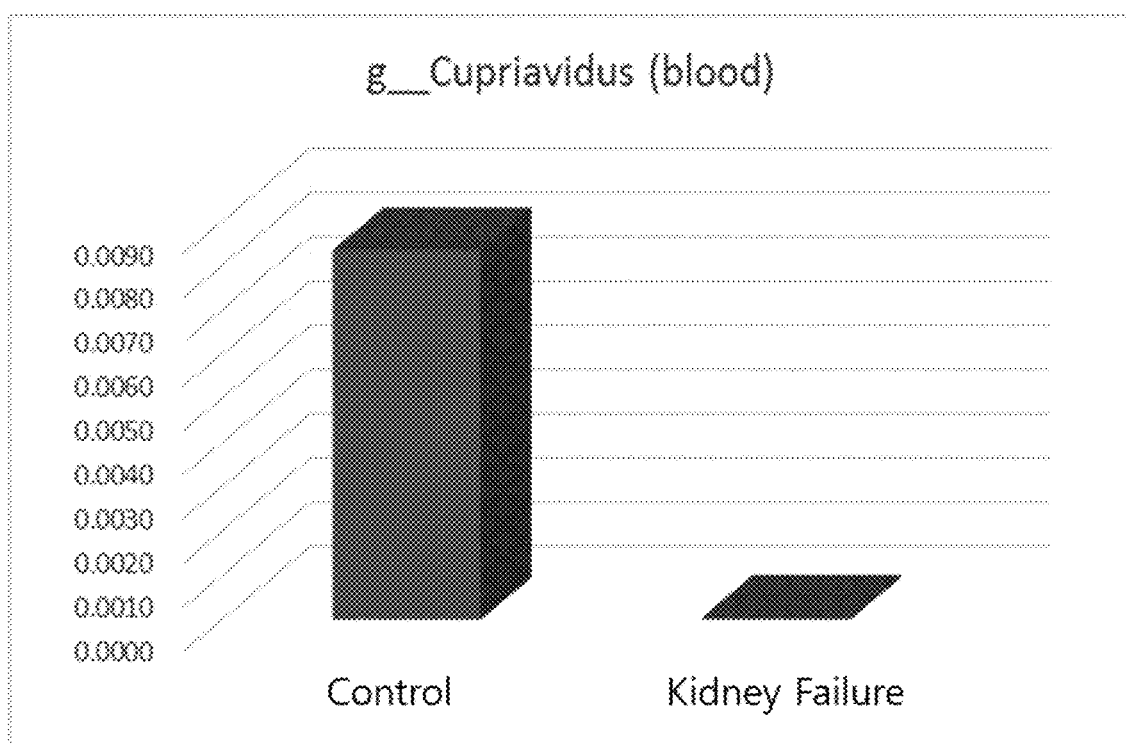
FIG. 16 is a result of comparing the distributions of vesicles derived from bacteria belonging to the genus *Cupriavidus* after metagenomic analysis of bacteria-derived vesicles present in the blood of kidney failure patients and a normal individuals.

Example 17. Metagenomic Analysis of Vesicles Derived from Bacteria in Blood of Patient with Kidney Failure Genes were extracted from vesicles present in blood samples of 32 kidney failure patients and 32 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the blood from the patients with kidney failure as compared to the blood from the normal individuals (see Table 26 and FIG. 16).

TABLE 26

| Blood | Control | | Kidney Failure | | t-test | |
|---|---|---|---|---|---|---|
| Taxon | Mean | SD | Mean | SD | p-value | Ratio |
| g_*Cupriavidus* | 0.0084 | 0.0073 | 0.0001 | 0.0002 | 0.0001 | 0.01 |

Figure 17:
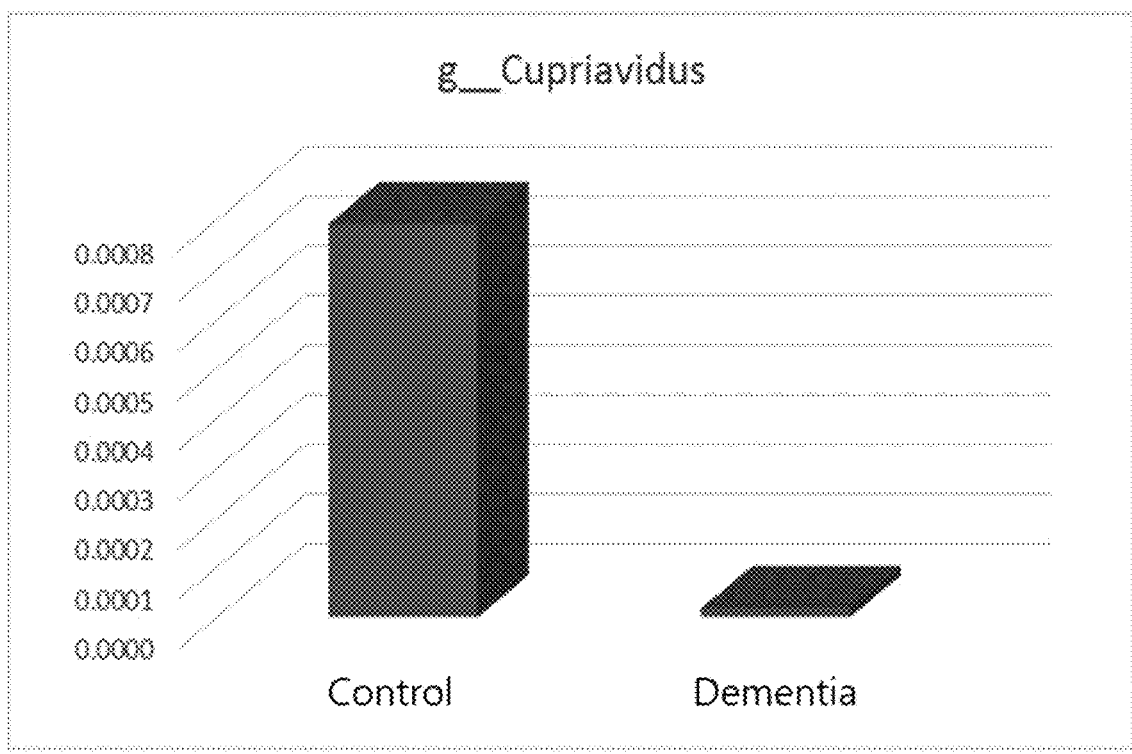
FIG. 17 is a result of comparing the distributions of vesicles derived from bacteria belonging to the genus *Cupriavidus* after metagenomic analysis of bacteria-derived vesicles present in the blood of dementia patients and a normal individuals.

Example 18. Metagenomic Analysis of Vesicles Derived from Bacteria in Blood of Patient with Dementia Genes were extracted from vesicles present in blood samples of 67 dementia patients and 70 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the blood from the patients with dementia as compared to the blood from the normal individuals (see Table 27 and FIG. 17).

TABLE 27

| Blood | Control | | Dementia | | t-test | |
|---|---|---|---|---|---|---|
| Taxon | Mean | SD | Mean | SD | p-value | Ratio |
| g_*Cupriavidus* | 0.0008 | 0.0023 | 0.0000 | 0.0002 | <0.0001 | 0.02 |

Figure 18:
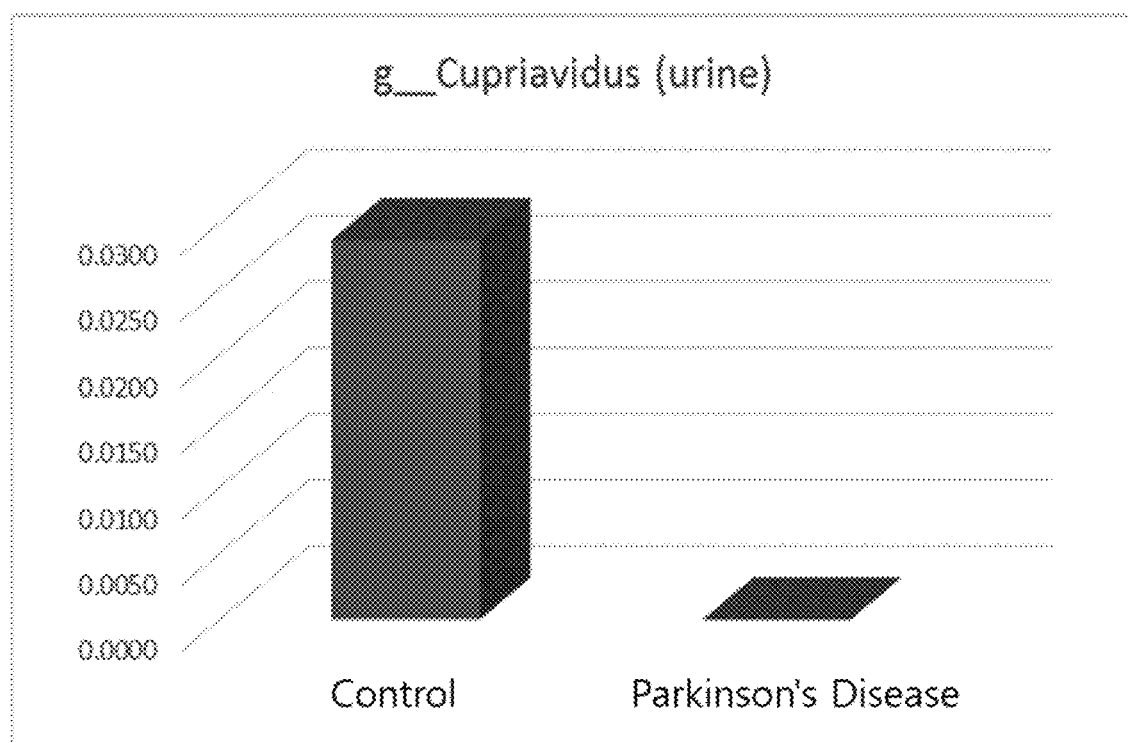
FIG. 18 is a result of comparing the distributions of vesicles derived from bacteria belonging to the genus *Cupriavidus* after metagenomic analysis of bacteria-derived vesicles present in the urine of Parkinson's disease patients and a normal individuals.

Example 19. Metagenomic Analysis of Vesicles Derived from Bacteria in Urine of Patient with Parkinson's Disease Genes were extracted from vesicles present in urine samples of 39 Parkinson's disease patients and 76 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the urine from the patients with Parkinson's disease as compared to the urine from the normal individuals (see Table 28 and FIG. 18).

TABLE 28

| Urine | Control | | Parkinson's Disease | | t-test | |
|---|---|---|---|---|---|---|
| Taxon | Mean | SD | Mean | SD | p-value | Ratio |
| g_Cupriavidus | 0.0287 | 0.1006 | 0.0000 | 0.0002 | 0.01 | 0.00 |

Figure 19:
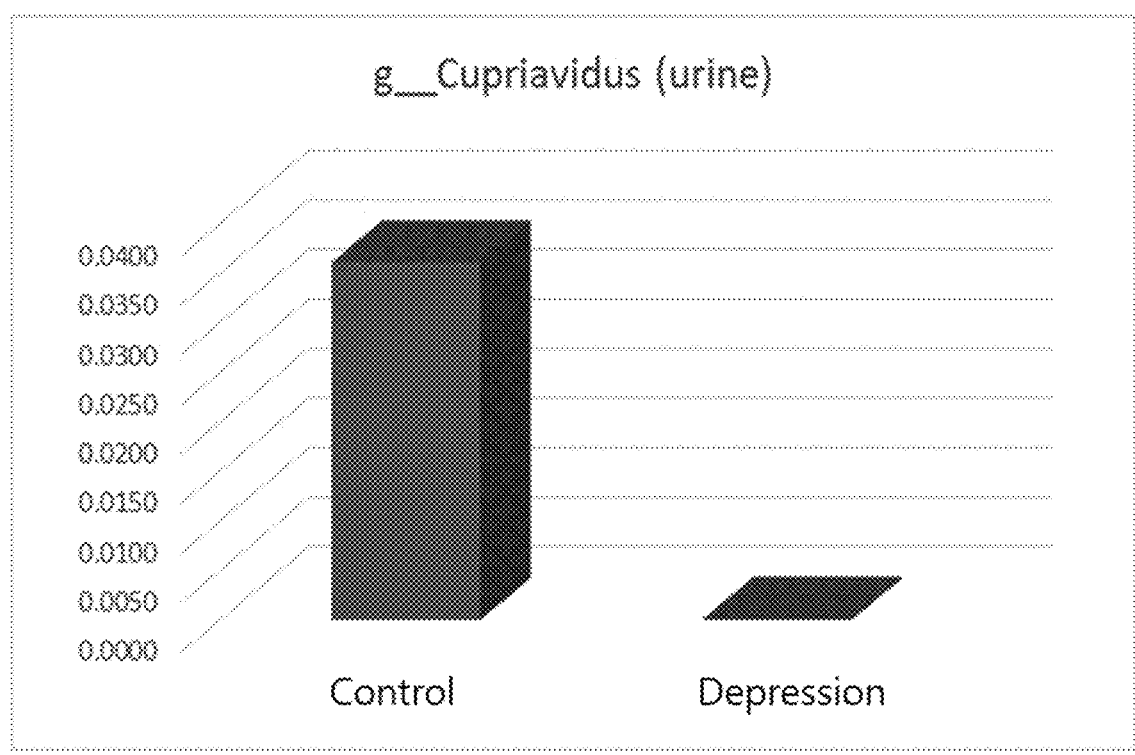
FIG. 19 is a result of comparing the distributions of vesicles derived from bacteria belonging to the genus *Cupriavidus* after metagenomic analysis of bacteria-derived vesicles present in the urine of depression patients and a normal individuals.

Example 20. Metagenomic Analysis of Vesicles Derived from Bacteria in Urine of Patient with Depression Genes were extracted from vesicles present in urine samples of 20 depression patients and 21 normal individuals, the two groups matched in gender and age, metagenomic analysis was performed thereon using the method of Example 2, and then the distribution of vesicles derived from bacteria belonging to the genus *Cupriavidus* was evaluated. As a result, it was confirmed that vesicles derived from belonging to the genus *Cupriavidus* were significantly decreased in the urine from the patients with depression as compared to the urine from the normal individuals (see Table 29 and FIG. 19).

TABLE 29

| Urine | Control | | Depression | | t-test | |
|---|---|---|---|---|---|---|
| Taxon | Mean | SD | Mean | SD | p-value | Ratio |
| g_Cupriavidus | 0.0361 | 0.0783 | 0.0001 | 0.0002 | 0.04 | 0.00 |

Example 21. Culturing of *Cupriavidus metallidurans* and Isolation of Vesicles from *Cupriavidus metallidurans*

The strain *C. metallidurans* was cultured, and then vesicles were isolated therefrom, followed by characterization thereof. The strain *C. metallidurans* was cultured in a tryptic soy broth (TSB) medium in an aerobic chamber at 28° C. until absorbance ($OD_{600}$) reached 1.0 to 1.5, and then sub-cultured in a Luria Bertani broth (LB) medium. Subsequently, a culture supernatant including the strain was recovered and centrifuged at 10,000 g and 4° C. for 20 minutes, and then the strain was removed and filtered through a 0.22 μm filter. The filtered supernatant was concentrated to a volume of 50 ml through microfiltration by using a MasterFlex pump system (Cole-Parmer, US) with a 100 kDa Pellicon 2 Cassette filter membrane (Merck Millipore, US). The concentrated supernatant was filtered once again with a 0.22-μm filter. Thereafter, proteins were quantified by using a BCA assay, and the following experiments were performed on the obtained vesicles.

Example 22. Anti-Inflammatory Effect of Vesicle Derived from *Cupriavidus metallidurans*

Figure 20:
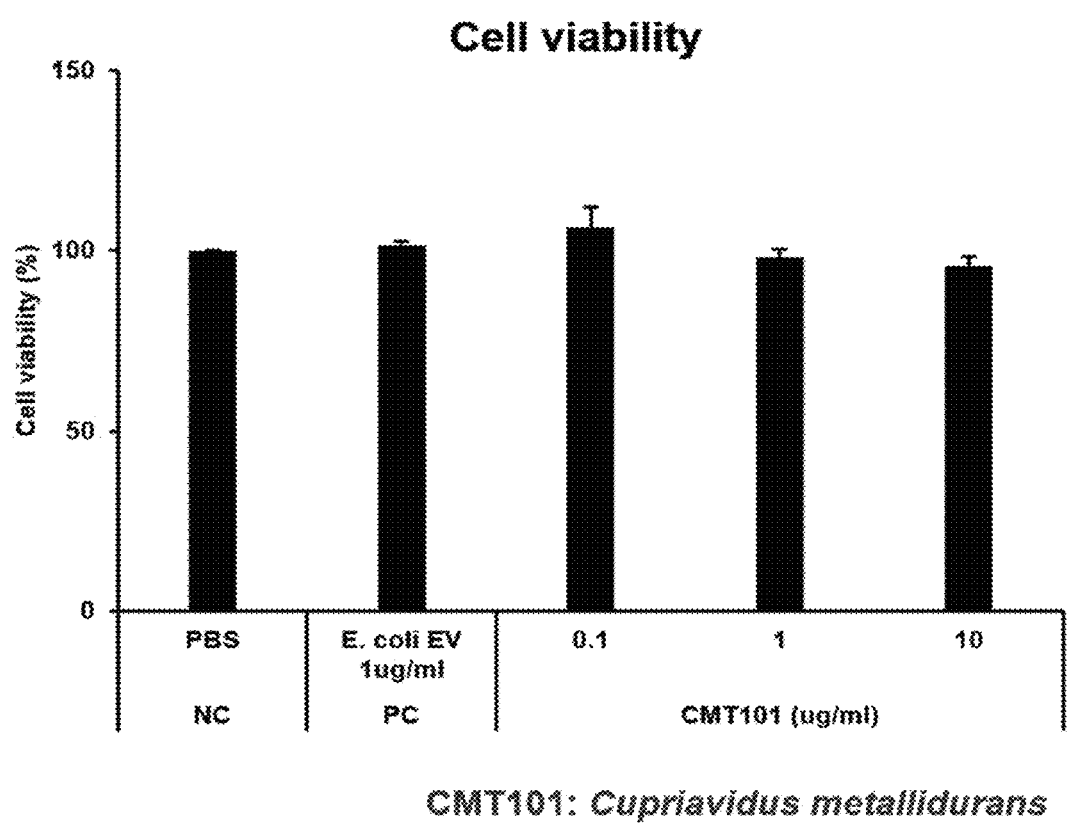
FIG. 20 illustrates results of evaluating the degree of apoptosis when vesicles derived from *Cupriavidus metallidurans* were administered to macrophages (Raw264.7), to evaluate an effect of the vesicles on apoptosis.

To investigate an effect of vesicles derived from *C. metallidurans* on apoptosis in inflammatory cells, Raw 264.7 cells, which is a mouse macrophage line, were treated with vesicles derived from *C. metallidurans* (*C. metallidurans* EVs) at various concentrations (0.1 μg/ml, 1 μg/ml, or 10 μg/ml), and then a cell viability test was performed thereon. More specifically, Raw 264.7 cells dispensed at a density of $4 \times 10^4$ cells/well were treated with various concentrations of vesicles derived from *C. metallidurans* in a Dulbeco's Modified Eagle's Medium (DMEM) serum-free medium in a 48-well cell culture plate and cultured for 12 hours. Subsequently, the cells were treated with EZ-CYTOX (Dogen, Korea) for 4 hours, and then absorbance at 450 nm was measured using a SpectraMax M3 microplate reader (Molecular Devies, USA). As a result, as illustrated in FIG. 20, it was confirmed that, when treated with the vesicles derived from *C. metallidurans*, apoptosis was not induced.

To evaluate an anti-inflammatory effect of vesicles derived from *C. metallidurans* based on the above result, the macrophage line was pretreated with vesicles derived from *C. metallidurans* at various concentrations (0.1 μg/ml, 1 μg/ml, or 10 μg/ml) for 12 hours, and then treated with 1 μg/ml of *E. coli*-derived EVs, which are pathogenic vesicles, and after 12 hours, the secretion of inflammatory cytokines was measured by ELISA. To perform ELISA, a capture antibody was diluted in phosphate buffered saline (PBS), 50 μl of the resulting solution was dispensed into a 96-well polystyrene plate in accordance with a working concentration, and then a reaction was allowed to occur therebetween at 4° C. overnight.

Next, the reaction product was washed three times with 100 μl of a PBST solution (PBS containing 0.05% Tween-20), and then 100 μl of an RD (PBS containing 1% BSA) solution was dispensed into the plate to perform blocking at room temperature for 1 hour, and a sample and a standard were dispensed in 50 μl aliquots in accordance with concentration and a reaction was allowed to occur therebetween at room temperature for 2 hours. Thereafter, the reaction product was washed three times with 100 μl of PBST, and then a detection antibody was diluted in RD, 50 μl of the resulting solution was dispensed in accordance with a working concentration, and a reaction was allowed to occur at room temperature for 2 hours. The reaction product was washed three times with 100 μl of PBST, and then Streptavidin-HRP (R&D System, USA) was diluted in RD to 1/40, 50 μl of the resulting solution was dispensed, and a reaction was allowed to occur at room temperature for 20 minutes.

Lastly, the reaction product was washed three times with 100 μl of PBST, and then 50 μl of a TMB substrate (SurModics, USA) was dispensed and, after 5 to 20 minutes, when color development progressed, 50 μl of a 1 M sulfuric acid solution was dispensed to terminate the reaction, and absorbance at 450 nm was measured using a SpectraMax M3 microplate reader (Molecular Devices, USA).

Figure 21:
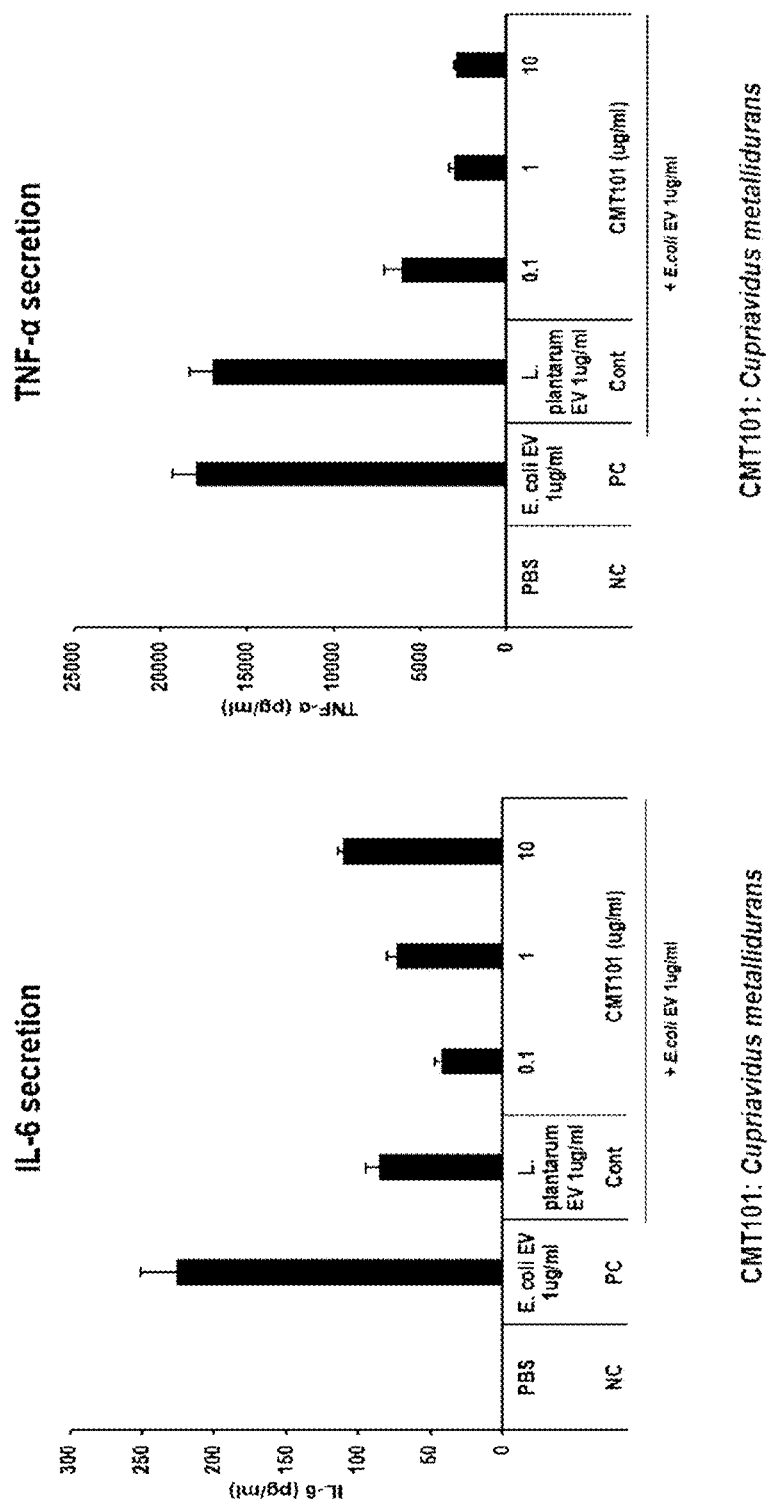
FIG. 21 illustrates results of evaluating an effect of vesicles derived from bacteria belonging to the genus *Cupriavidus* on the secretion of IL-6 and TNF-α, which are inflammatory mediators, by *E. coli* vesicles, after pretreatment of the vesicles prior to treatment with *E. coli* EVs, which are pathogenic vesicles, to evaluate an effect of vesicles derived from *Cupriavidus metallidurans* on anti-inflammation and immune regulation.

As a result, as illustrated in FIG. 21, it was confirmed that, when pretreated with vesicles derived from *C. metallidurans*, the secretion of IL-6 and TNF-α by *E. coli*-derived EVs was significantly inhibited. In particular, it was confirmed that the TNF-α secretion inhibitory effect by pretreatment with the vesicles derived from *C. metallidurans* was significantly greater than that by pretreatment with *Lactobacillus plantarum*-derived vesicles, which is a useful microorganism control. These results indicate that vesicles derived from *C. metallidurans* are capable of effectively inhibiting inflammatory responses induced by pathogenic vesicles such as *E. coli*-derived EVs.

Example 23. Effect of Heat or Acid Treatment on Anti-Inflammatory Activity of Vesicles Derived from *Cupriavidus metallidurans*

The anti-inflammatory effect of vesicles derived from *Cupriavidus metallidurans* was confirmed through Example 22, and furthermore, the stability of the vesicles and the properties of the active ingredient were examined in detail. To evaluate an anti-inflammatory effect, Raw 264.7 cells, which are a mouse macrophage line, were pretreated with vesicles derived from *Cupriavidus metallidurans* which had been boiled at 100° C. for 10 minutes or treated with acid (pH 2.0) for 10 minutes.

Figure 22:
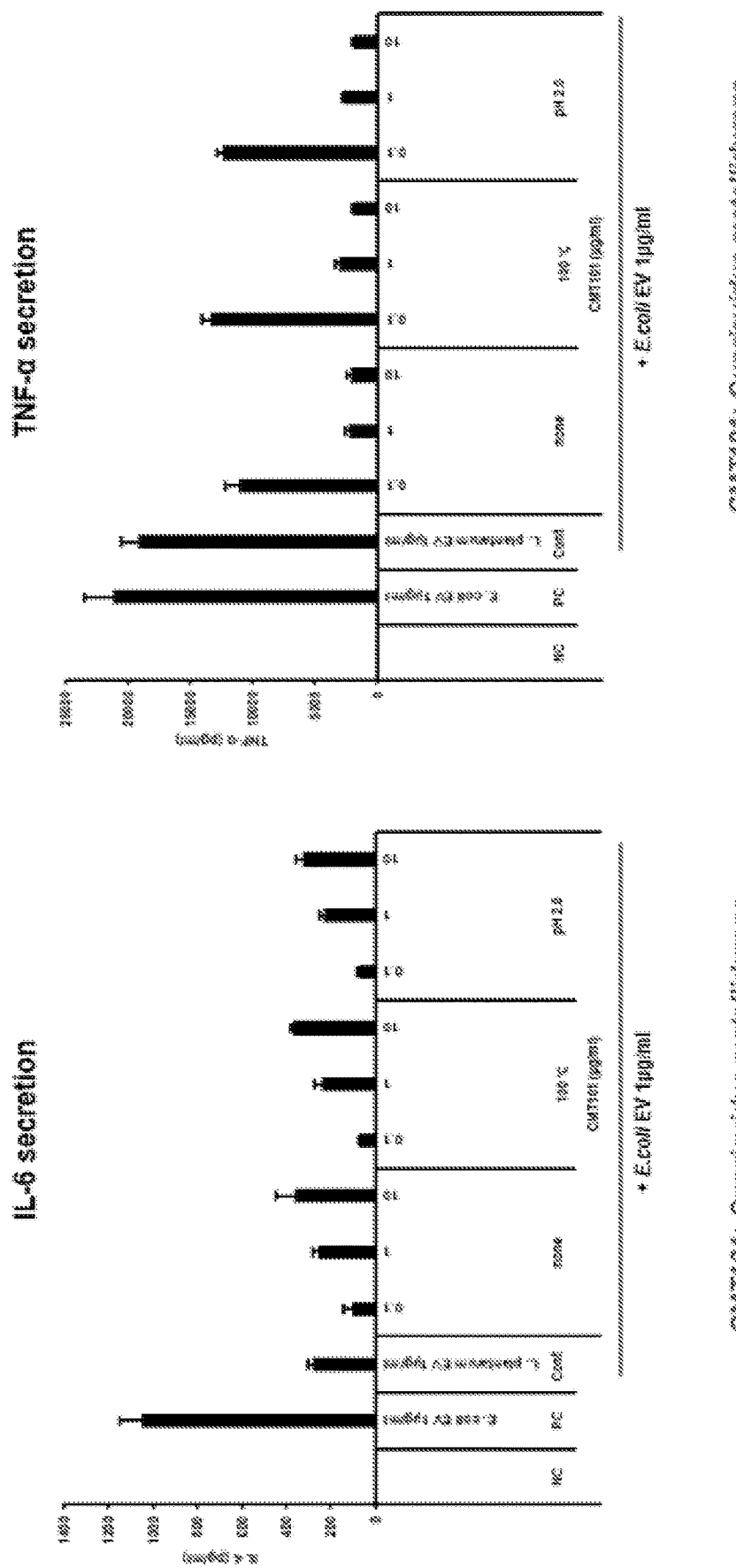
FIG. 22 illustrates results of the stability of the vesicles derived from *Cupriavidus metallidurans* and the properties of the active ingredient were examined.

As a result, it was confirmed that, although the vesicles were boiled at 100° C. or treated with acid, the anti-inflammatory effect of the vesicles derived from *Cupriavidus metallidurans* was maintained (see FIG. 22). This means that vesicles derived from *Cupriavidus metallidurans* are stable against high temperature and acid, and components of the vesicles derived from *Cupriavidus metallidurans* exhibiting an anti-inflammatory effect are not protein components.

Example 24. Anti-Cancer Effect of Vesicle Derived from *Cupriavidus metallidurans*

Figure 23:
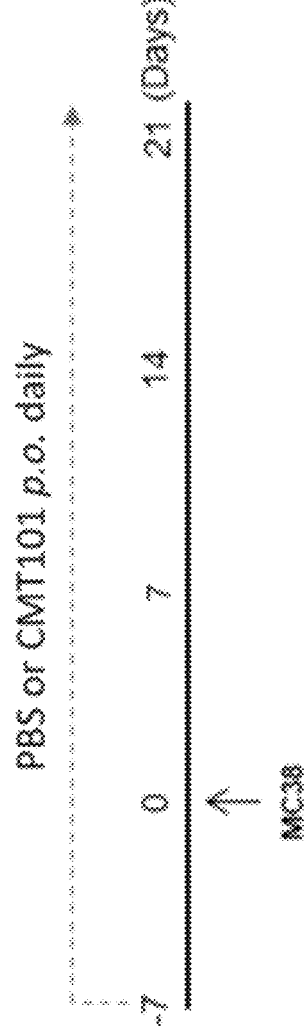
FIG. 23 is a protocol of administering vesicles derived from *Cupriavidus metallidurans* to mice in order to evaluate the anticancer efficacy of vesicles derived from *Cupriavidus metallidurans*.

Anti-cancer effects of vesicles derived from *C. metallidurans* were investigated based on the Examples. For this purpose, as illustrated in FIG. 23, a cancer model was prepared by orally administering vesicles derived from isolated strains of *Cupriavidus metallidurans* (CMT101) to 6-week old C57BL/6 mice, and subcutaneously injecting a cancer cell line (MC38 cell) on day 7 after administration. After administration of the cancer cell line, the vesicles derived from *C. metallidurans* were orally administered daily, and the sizes of cancer tissues were measured until day 21.

Figure 24:
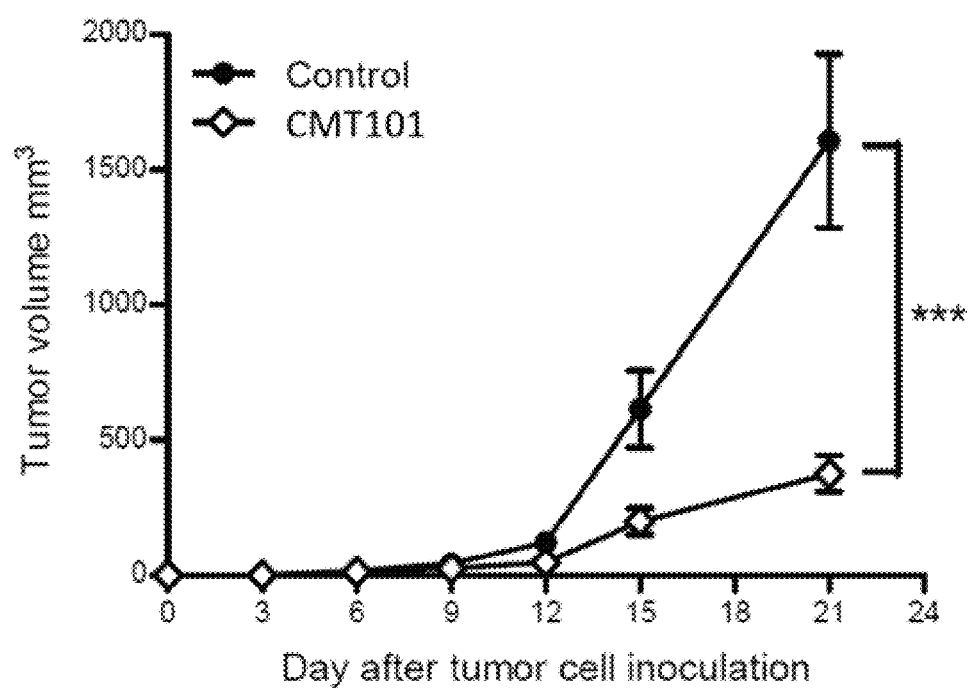
FIG. 24 illustrates result of evaluating effects of cancer cells on tumorigenesis by administering *Cupriavidus metallidurans* vesicles orally (PO) in order to evaluate the anticancer efficacy of vesicles derived from *Cupriavidus metallidurans*.

As a result, as illustrated in FIG. 24, the sizes of cancer tissues were decreased in mice to which the vesicles were orally administered as compared to a group to which PBS was orally administered, which is a control (***$p<0.001$). This means that when vesicles derived from *C. metallidurans* are administered, the growth of cancer tissues may be efficiently suppressed.

Example 25. Immunological Mechanism of Vesicles Derived from *Cupriavidus metallidurans*

Based on Example 24, the immunological mechanism of anticancer efficacy of vesicles derived from *Cupriavidus metallidurans* was investigated. To this end, tumors were extracted from a mouse cancer model orally administered vesicles derived from *Cupriavidus metallidurans* to perform immune cell analysis. More specifically, tumors were extracted from a control group mice administered only PBS and experimental group mice administered vesicles derived from *Cupriavidus metallidurans* and finely cut, and then collagenase D and DNase I were added thereto, followed by incubation at 37° C. for 45 minutes while being continuously mixed. After 45 minutes, the resultant mixture was allowed to pass through a 70 μm strainer and then centrifuged (1,300 rpm, 5 minutes, 4° C.) to collect a cell pellet. The collected cell pellet was released with 30% Percoll diluted with HBSS, and then put on 70% Percoll, followed by further centrifugation (2,000 rpm, 25 minutes, 25° C.). Tumor-infiltrating immune cells collected at the interface between 70% Percoll and 30% Percoll were separated using a pipette and 10 ml of a preparation buffer was added thereto. The cells were counted and centrifuged (1,300 rpm, 5 minutes, 4° C.) to obtain a cell pellet, and then the agglomerated cells were released well with an FACS buffer, and for FACS antibody staining, the concentration of the cells was adjusted to $10 \times 10^6$ cells/ml. After the FACS antibody staining, the stained cells were analyzed using LSRFortessa X-20.

Figure 25:
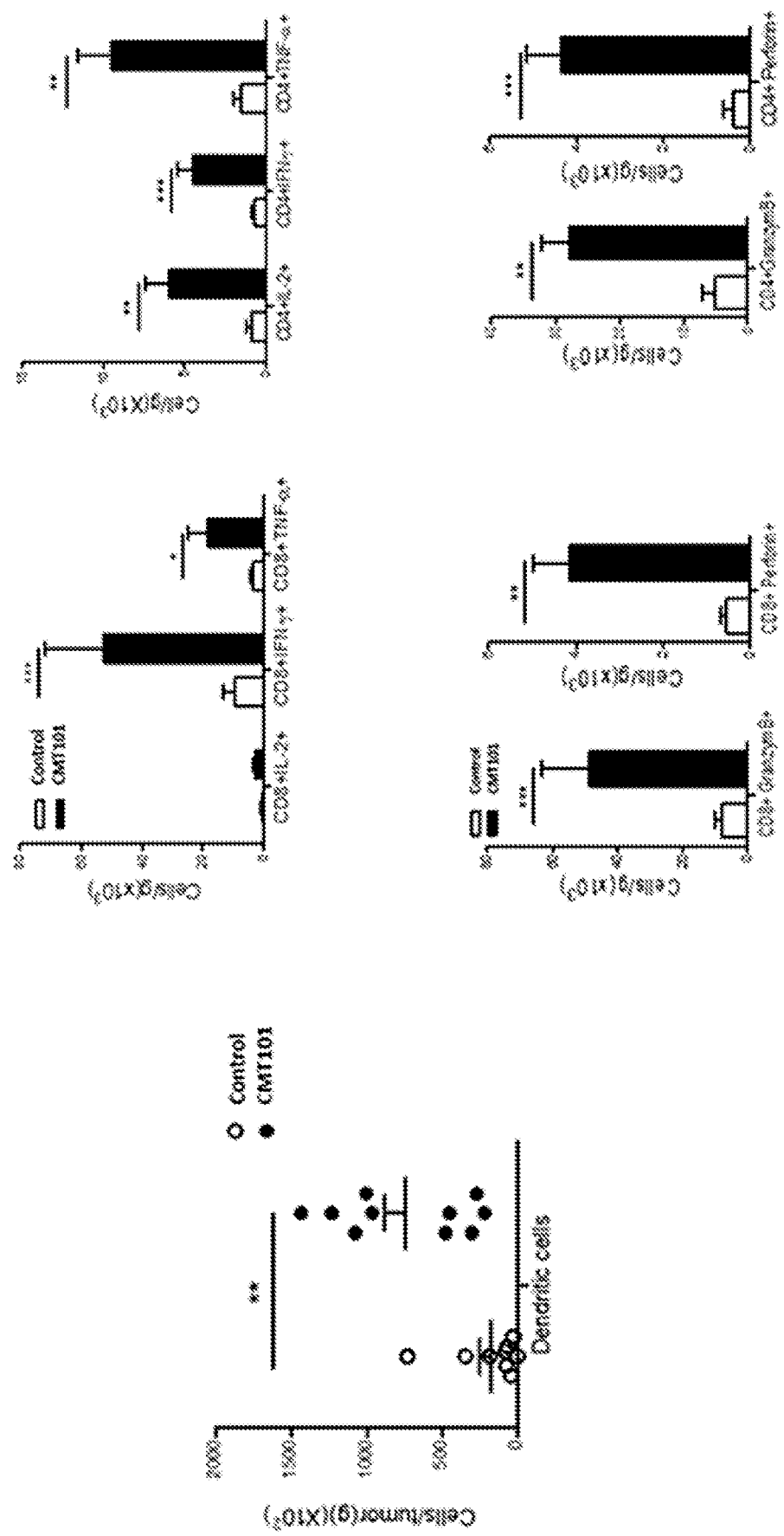
FIG. 25 illustrates result of cofirming the immunological mechanism of anticancer efficacy of vesicles derived from *Cupriavidus metallidurans* through FACS anaylsis.
Figure 26:
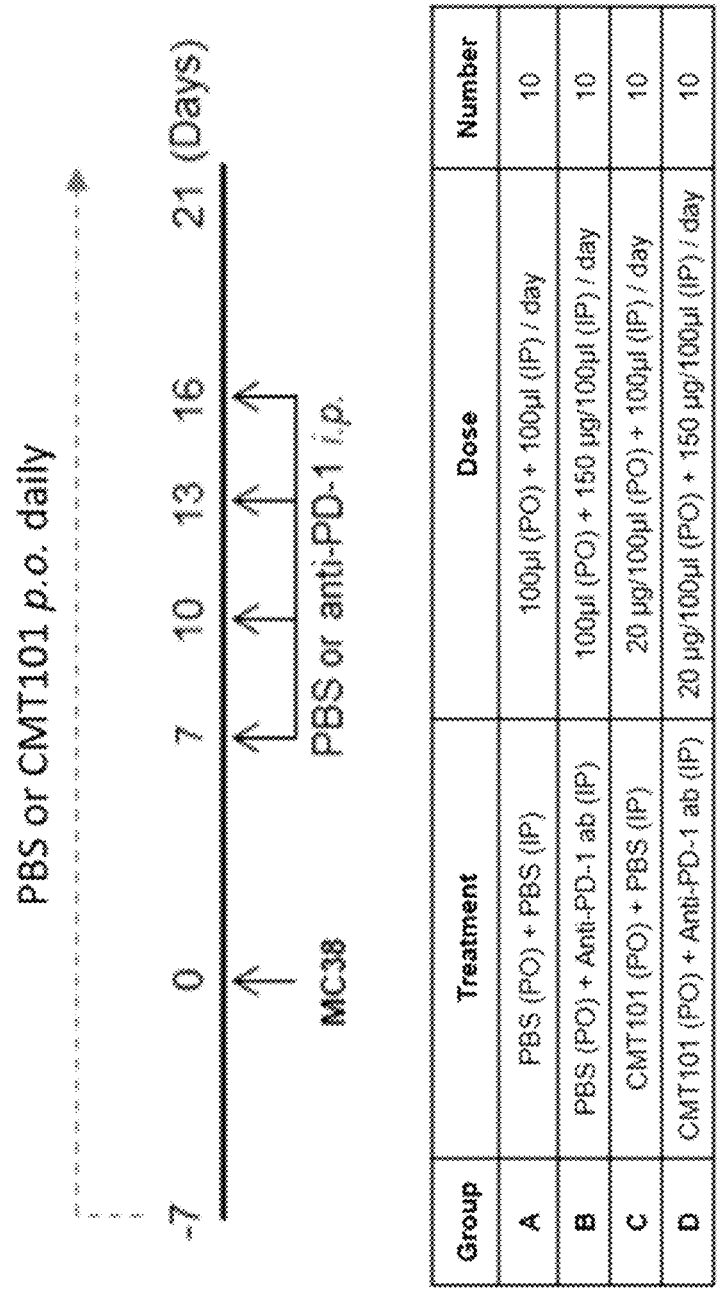
FIG. 26 is a protocol of co-administering anti-PD-1 antibody and vesicles derived from *Cupriavidus metallidurans* to mice in order to evaluate the anticancer efficacy of co-administration of immune check point blocking agent and vesicles derived from *Cupriavidus metallidurans*.

As a result, as illustrated in FIG. 25, it was confirmed that dendritic cells, which are involved in the presentation of antigens to T cells and activation thereof, were more infiltrated into tumor tissues of groups administered vesicles derived from *Cupriavidus metallidurans* than in the control. It was also confirmed that CD4+ T cells and CD8+ T cells expressing IFN-γ and TNF-α cytokines, which are vitally involved in an anti-cancer immune action, were infiltrated more into tumor tissues of groups administered vesicles derived from *Cupriavidus metallidurans* than in the control. While there was no significant different in the number of CD8+ T cells expressing IL-2 between the tumor tissues of groups administered vesicles derived from *Cupriavidus metallidurans* and the control, it was observed that a greater number of CD4+ T cells expressing IL-2 was infiltrated into the tumor tissues compared to the control. Additionally, it was confirmed that a greater number of cells expressing Granzyme B and Perforin in both CD4+ T cells and CD8+ T cells was observed in the tumor tissues administered vesicles derived from *Cupriavidus metallidurans* than in the control. These results mean that vesicles derived from *Cupriavidus metallidurans* increase the migration of dendritic cells and activated T cells to tumor tissue or increase the division and activity of T cells through dendritic cells in tumor tissue, thereby inducing an anti-cancer immune action, and accordingly, can suppress the growth of cancer tissue. Through the results, it was confirmed that the vesicles derived from *Cupriavidus metallidurans* can be used as a cancer cancer immunotherapy regimen Example 26. Effect of Co-Administration of Vesicles Derived from *Cupriavidus metallidurans* and Immune Anticancer Agent Based on Example 25, the effect of co-administration of an anti-PD-1 antibody as an immune anticancer agent and vesicles derived from *Cupriavidus metallidurans* was investigated. To this end, as illustrated in FIG. 26, vesicles derived from a *Cupriavidus metallidurans* strain (CMT101) were orally administered to 6-week-old C57BL/6J mice, and 7 days after the oral administration started, a cancer cell line (MC38 cells) was subcutaneously injected once to produce a cancer model. After the cancer cell line administration, the vesicles derived from a *Cupriavidus metallidurans* strain was orally administered daily up to day 21, and the anti-PD-1 antibody was intraperitoneally injected from day 7 after the cancer cell line transplantation a total of four times at three day intervals, and the size of cancer tissues was measured up to day 21.

Figure 27:
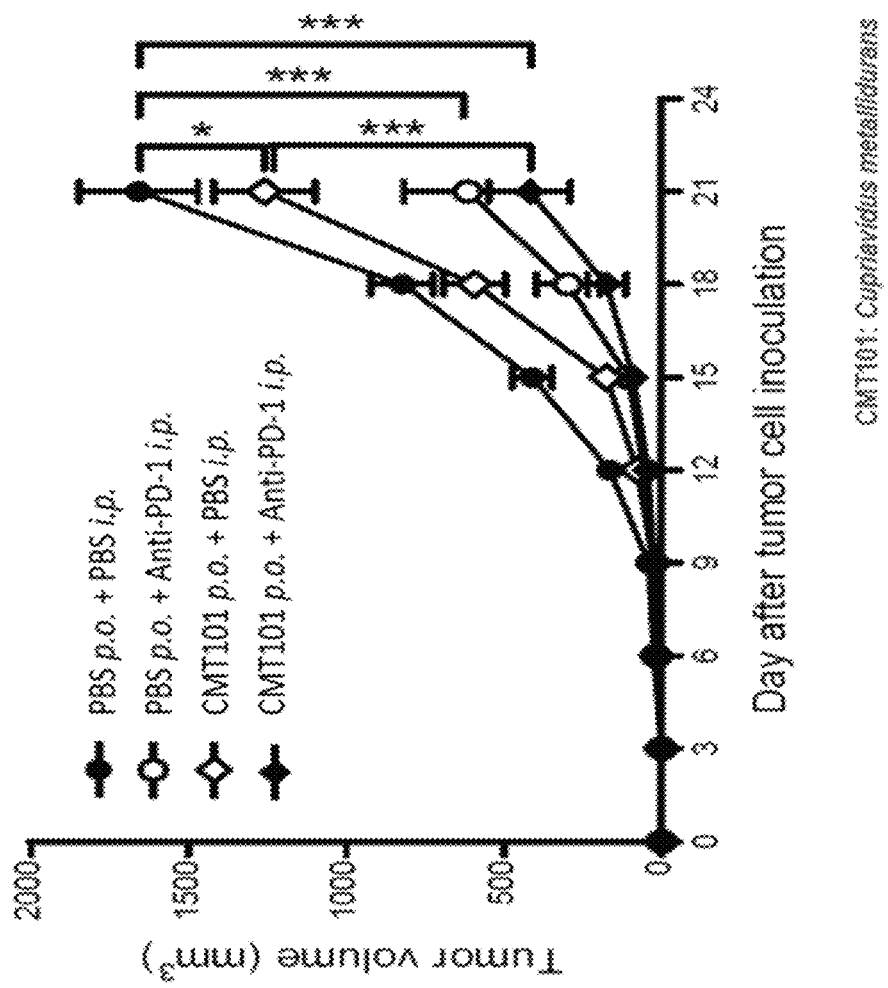
FIG. 27 illustrates result of evaluating effects of cancer cells on tumorigenesis by co-administering anti-PD-1 antibody and *Cupriavidus metallidurans* vesicles in order to evaluate the anticancer efficacy of co-administration.

As a result, as illustrated in FIG. 27, the size of cancer tissue was reduced in all of a group administered only vesicles derived from *Cupriavidus metallidurans*, a group administered an anti-PD-1 antibody alone, and a group co-administered vesicles derived from *Cupriavidus metallidurans* and the anti-PD-1 antibody, compared to a control administered phosphate buffered saline (PBS), and in particular, the size of cancer tissue was further reduced in the case of co-administration of the vesicles derived from *Cupriavidus metallidurans* and the anti-PD-1 antibody. These results mean that, even upon co-administration with an immune anticancer agent, vesicles derived from *Cupriavidus metallidurans* can efficiently suppress the growth of cancer tissue.

The above-described description of the present invention is provided for illustrative purposes, and those of ordinary skill in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

Vesicles derived from bacteria belonging to the genus *Cupriavidus* according to the present invention can be used not only in a method of diagnosing gastric cancer, colon cancer, pancreatic cancer, cholangiocarcinoma, breast cancer, ovarian cancer, bladder cancer, prostate cancer, head and neck cancer, lymphoma, cardiomyopathy, atrial fibrillation, variant angina, chronic obstructive pulmonary disease, stroke, diabetes, kidney failure, dementia, Parkinson's disease, or depression, but also as a composition for preventing, alleviating, or treating the above-described diseases, and thus are expected to be effectively used in the related medical and food industrial fields.

The invention claimed is:

1. A method of suppressing tumor growth, the method comprising administering to a subject having a tumor a composition comprising an effective amount of vesicles derived from bacteria belonging to *Cupriavidus metallidurans*.

2. The method of claim 1, wherein the composition is a pharmaceutical composition or a food composition.

3. The method of claim 1, wherein the vesicles are naturally or artificially secreted from the bacteria belonging to *Cupriavidus metallidurans*.

4. The method of claim 1, wherein the composition is an inhalant composition.

5. The method of claim 1, wherein the tumor is selected from the group consisting of colon cancer, gastric cancer, pancreatic cancer, cholangiocarcinoma, breast cancer, ovarian cancer, bladder cancer, prostate cancer, head and neck cancer, and lymphoma.

6. The method of claim 1, wherein the composition further comprises an immune check point blocking agent.

7. The method of claim 6, wherein the immune check point blocking agent is selected from the group consisting of anti-PD-1, anti-PD-L1, anti-CTLA-4, anti-B7-H4, anti-B7-

H1, anti-LAG3, BTLA, anti-Tim3, anti-B7-DC, anti-CD160, anti-4-1BB, anti-OX40, anti-CD27, and CD40 agonist antibodies.

8. The method of claim 1, wherein the vesicles have an average diameter of 10 to 200 nm.

* * * * *

SEQUENCE LISTING

```
<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: 16S_V3_F
<220> FEATURE:
<221> NAME/KEY: misc_feature
<222> LOCATION: (42)
<223> OTHER INFORMATION: a, c, g or t

<400> SEQUENCE: 1
tcgtcggcag cgtcagatgt gtataagaga cagcctacgg gnggcwgcag          50

<210> SEQ ID NO 2
<211> LENGTH: 55
<212> TYPE: DNA
<213> ORGANISM: Artificial Sequence
<220> FEATURE:
<223> OTHER INFORMATION: 16S_V4_R

<400> SEQUENCE: 2
gtctcgtggg ctcggagatg tgtataagag acaggactac hvgggtatct aatcc    55
```